United States Patent
Moya et al.

(10) Patent No.: US 9,376,464 B2
(45) Date of Patent: *Jun. 28, 2016

(54) PURIFICATION OF PROTEINS

(71) Applicant: EMD Millipore Corporation, Billerica, MA (US)

(72) Inventors: Wilson Moya, Concord, MA (US); Jad Jaber, Nashua, NH (US)

(73) Assignee: EMD Millipore Corporation, Billerica, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/747,495

(22) Filed: Jan. 23, 2013

(65) Prior Publication Data

US 2013/0137860 A1 May 30, 2013

Related U.S. Application Data

(63) Continuation of application No. 12/004,319, filed on Dec. 20, 2007, now Pat. No. 8,362,217.

(60) Provisional application No. 60/876,330, filed on Dec. 21, 2006.

(51) Int. Cl.
*C07K 1/30* (2006.01)
*C07K 1/32* (2006.01)

(52) U.S. Cl.
CPC .... *C07K 1/32* (2013.01); *C07K 1/30* (2013.01)

(58) Field of Classification Search
None
See application file for complete search history.

(56) References Cited

U.S. PATENT DOCUMENTS

| | | |
|---|---|---|
| 2,923,669 A | 2/1960 | Poitras |
| 3,211,645 A | 10/1965 | Ferrari |
| 3,556,302 A | 1/1971 | Agranant |
| 3,565,973 A | 2/1971 | Michaels |
| 3,632,507 A | 1/1972 | Witt |
| 3,702,806 A | 11/1972 | Oliva |
| 3,737,377 A | 6/1973 | Sternberg |
| 3,859,212 A | 1/1975 | Smalley et al. |
| 3,968,037 A | 7/1976 | Morgan et al. |
| 4,045,377 A | 8/1977 | Pearson |
| 4,055,469 A | 10/1977 | Snoke et al. |
| 4,200,695 A | 4/1980 | Chong et al. |
| 4,215,198 A | 7/1980 | Gordon |
| 4,305,829 A | 12/1981 | Kelsey et al. |
| 4,317,726 A | 3/1982 | Shepel |
| 4,359,537 A | 11/1982 | Chong |
| 4,371,674 A | 2/1983 | Hertel et al. |
| 4,380,590 A | 4/1983 | Chong |
| 4,382,028 A | 5/1983 | Paget |
| 4,450,078 A | 5/1984 | Walker et al. |
| 4,515,893 A | 5/1985 | Kung et al. |
| 4,528,933 A | 7/1985 | Allen |
| 4,536,294 A | 8/1985 | Guillet et al. |
| 4,676,980 A | 6/1987 | Segal et al. |
| 4,780,409 A | 10/1988 | Monji et al. |
| 4,816,567 A | 3/1989 | Cabilly et al. |
| 4,828,701 A | 5/1989 | Cussler |
| 4,839,046 A | 6/1989 | Chandler |
| 4,863,613 A | 9/1989 | Johnson et al. |
| 4,904,385 A | 2/1990 | Wessling et al. |
| 4,912,032 A | 3/1990 | Hoffman et al. |
| 4,925,785 A | 5/1990 | Wang et al. |
| 4,968,435 A | 11/1990 | Neff et al. |
| 5,003,047 A | 3/1991 | Yarmush et al. |
| 5,047,511 A | 9/1991 | Mehrotra |
| 5,091,178 A | 2/1992 | Hellstrom et al. |
| 5,091,313 A | 2/1992 | Chang |
| 5,116,754 A | 5/1992 | Fraser et al. |
| 5,139,031 A | 8/1992 | Guirguis |
| 5,152,903 A | 10/1992 | Neff et al. |
| 5,164,057 A | 11/1992 | Mori et al. |
| 5,171,450 A | 12/1992 | Hoots |
| 5,208,161 A | 5/1993 | Saunders et al. |
| 5,238,545 A | 8/1993 | Yoshioka et al. |

(Continued)

FOREIGN PATENT DOCUMENTS

| | | |
|---|---|---|
| EP | 0162034 B1 | 11/1990 |
| EP | 0534016 A1 | 3/1993 |

(Continued)

OTHER PUBLICATIONS

Giga-Hama et al. "Expression system for foreign genes using the fission yeast *Schizosaccharomyces pombe*" Biotechnol. Appl. Biochem. (1999), 30, 235-244.*

Journal of Biotechnology, vol. 128, No. 4, Mar. 2007, pp. 813-823, "The use of chitosan as a flocculant in mammalian cell culture dramatically improves clarification throughput without adversely impacting monoclonal antibody recovery", Riske, et al.

Biotechnol. Prog, vol. 24, No. 3, May/Jun. 2008, pp. 488-495, "Advances in Primary Recovery: Centrifugation and Membrane Technology", Roush, et al.

Anal. Chem., vol. 71, No. 20, Oct. 1999, pp. 4506-4512, "Concentration of Hydrophobic Organic Compounds by Polymer-Mediated Extraction", Saitoh, et al.

(Continued)

*Primary Examiner* — Daniel E Kolker
*Assistant Examiner* — James Rogers
(74) *Attorney, Agent, or Firm* — Nields, Lemack & Frame, LLC

(57) ABSTRACT

The present invention relates to a selectively soluble polymer capable of binding to a desired biomolecules in a mixture containing various biological materials and the methods of using such a polymer to purify a biomolecule from such a mixture. The polymer is soluble in the mixture under a certain set of process conditions such as pH or temperature and/or salt concentration and is rendered insoluble and precipitates out of solution upon a change in the process conditions. The polymer is capable of binding to the desired biomolecule (protein, polypeptide, etc) and remains capable of binding to that biomolecule even after the polymer is precipitated out of solution. The precipitate can then be filtered out from the remainder of the stream and the desired biomolecule is recovered such as by elution and further processed.

4 Claims, 4 Drawing Sheets

(56) References Cited

U.S. PATENT DOCUMENTS

Figure 1:
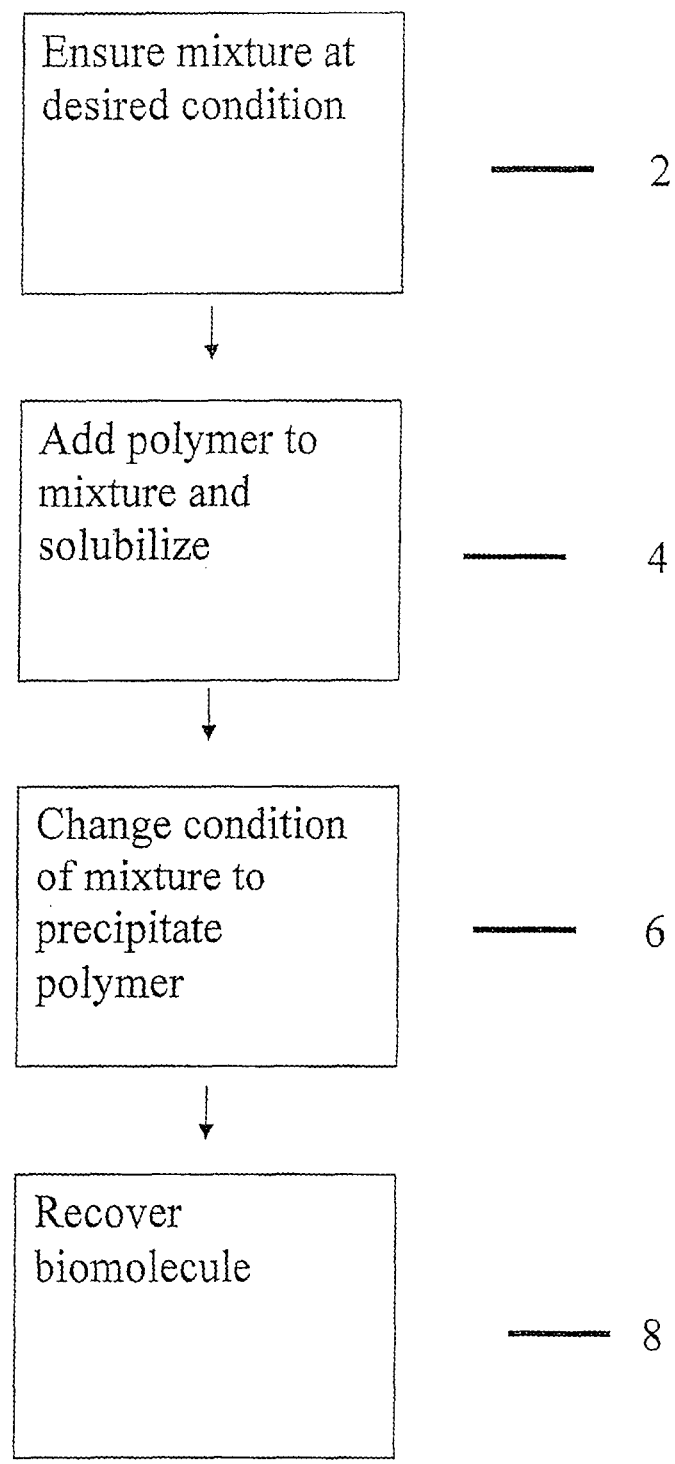

| Patent Number | Date | Inventor(s) |
|---|---|---|
| 5,258,122 A | 11/1993 | Ha et al. |
| 5,324,787 A | 6/1994 | Pinschmidt, Jr. et al. |
| 5,340,865 A | 8/1994 | Neff et al. |
| 5,342,581 A | 8/1994 | Sanadi |
| 5,354,481 A | 10/1994 | Neff et al. |
| 5,354,801 A | 10/1994 | O'Toole |
| 5,374,971 A | 12/1994 | Clapp et al. |
| 5,430,110 A | 7/1995 | Ahlers et al. |
| 5,512,480 A | 4/1996 | Sandstrom et al. |
| 5,525,519 A | 6/1996 | Woiszwillo |
| 5,573,675 A | 11/1996 | Sommese et al. |
| 5,599,719 A | 2/1997 | Woiszwillo et al. |
| 5,622,700 A | 4/1997 | Jardieu et al. |
| 5,622,857 A | 4/1997 | Goffe |
| 5,672,347 A | 9/1997 | Aggarwal et al. |
| 5,684,107 A | 11/1997 | Schneider et al. |
| 5,693,762 A | 12/1997 | Queen et al. |
| 5,714,338 A | 2/1998 | Wai Fei et al. |
| 5,721,108 A | 2/1998 | Robinson et al. |
| 5,725,856 A | 3/1998 | Hudziak et al. |
| 5,728,559 A | 3/1998 | Nilsson et al. |
| 5,733,507 A | 3/1998 | Zakim |
| 5,736,137 A | 4/1998 | Anderson et al. |
| 5,739,383 A | 4/1998 | Yoon et al. |
| 5,770,358 A | 6/1998 | Dower et al. |
| 5,807,489 A | 9/1998 | Farinato et al. |
| 5,840,804 A | 11/1998 | Carl et al. |
| 5,840,851 A | 11/1998 | Plomer et al. |
| 5,846,816 A | 12/1998 | Forth |
| 5,879,564 A | 3/1999 | Farinato |
| 5,929,214 A | 7/1999 | Peters et al. |
| 5,994,560 A | 11/1999 | Yoon et al. |
| 5,998,588 A | 12/1999 | Hoffman et al. |
| 6,024,955 A | 2/2000 | Asano et al. |
| 6,127,526 A | 10/2000 | Blank |
| 6,133,047 A | 10/2000 | Elaissari et al. |
| 6,139,746 A | 10/2000 | Kopf |
| 6,147,176 A | 11/2000 | Neff et al. |
| 6,153,104 A | 11/2000 | Robertson |
| 6,191,242 B1 | 2/2001 | Ryles et al. |
| 6,197,522 B1 | 3/2001 | Keller et al. |
| 6,221,655 B1 | 4/2001 | Fung et al. |
| 6,245,555 B1 | 6/2001 | Curtis |
| 6,258,275 B1 | 7/2001 | Freitag et al. |
| 6,294,622 B1 | 9/2001 | Barajas et al. |
| 6,300,142 B1 | 10/2001 | Andrewes et al. |
| 6,307,013 B1 | 10/2001 | Chivers |
| 6,358,730 B1 | 3/2002 | Kane |
| 6,367,749 B2 | 4/2002 | Valiulis |
| 6,372,141 B1 | 4/2002 | Okano et al. |
| 6,374,684 B1 | 4/2002 | Dority |
| 6,420,487 B1 | 7/2002 | Vaidya et al. |
| 6,454,950 B1 | 9/2002 | Tjerneld et al. |
| 6,521,341 B1 | 2/2003 | Elaissari et al. |
| 6,534,633 B1 | 3/2003 | Weidanz et al. |
| 6,538,089 B1 | 3/2003 | Samra et al. |
| 6,544,424 B1 | 4/2003 | Shevitz |
| 6,565,872 B2 | 5/2003 | Wu et al. |
| 6,582,926 B1 | 6/2003 | Chilkoti |
| 6,638,918 B2 | 10/2003 | Davison et al. |
| 6,641,735 B1 | 11/2003 | Yoshizako et al. |
| 6,673,598 B1 | 1/2004 | Akers et al. |
| 6,689,836 B2 | 2/2004 | Vaidya et al. |
| 6,706,187 B1 | 3/2004 | Okano et al. |
| 6,709,862 B2 | 3/2004 | Curtis |
| 6,716,593 B1 | 4/2004 | Robins et al. |
| 6,737,235 B1 | 5/2004 | Cros et al. |
| 6,765,081 B2 | 7/2004 | Lin et al. |
| 6,770,758 B2 | 8/2004 | Pan et al. |
| 6,805,793 B2 | 10/2004 | Yoshizako et al. |
| 6,821,515 B1 | 11/2004 | Cleland et al. |
| 6,830,670 B1 | 12/2004 | Viovy et al. |
| 6,852,819 B2 | 2/2005 | Ohnishi et al. |
| 6,858,694 B2 | 2/2005 | Ohnishi et al. |
| 6,863,437 B2 | 3/2005 | Ohnishi et al. |
| 6,867,268 B2 | 3/2005 | Vaidya et al. |
| 6,926,832 B2 | 8/2005 | Collins et al. |
| 6,956,077 B1 | 10/2005 | Akiyama et al. |
| 6,967,085 B1 | 11/2005 | Hughes et al. |
| 6,974,660 B2 | 12/2005 | Manias et al. |
| 7,001,953 B2 | 2/2006 | Chen et al. |
| 7,011,930 B2 | 3/2006 | Manias et al. |
| 7,012,136 B2 | 3/2006 | Yamanaka et al. |
| 7,052,917 B1 | 5/2006 | Ohnishi et al. |
| 7,070,696 B2 | 7/2006 | Weir et al. |
| 7,083,948 B1 | 8/2006 | Sassenfeld et al. |
| 7,157,603 B2 | 1/2007 | Hilbrig |
| 7,160,971 B2 | 1/2007 | Mallapragada et al. |
| 7,169,908 B2 | 1/2007 | Lester et al. |
| 7,195,925 B2 | 3/2007 | Ohnishi et al. |
| 7,300,545 B2 | 11/2007 | Ohara et al. |
| 7,355,020 B2 | 4/2008 | Yamanaka et al. |
| 7,377,686 B2 | 5/2008 | Hubbard |
| 7,393,698 B2 | 7/2008 | Furukawa et al. |
| 7,422,724 B1 | 9/2008 | Manginell et al. |
| 7,429,458 B2 | 9/2008 | Chilkoti |
| 7,442,515 B2 | 10/2008 | Ratner et al. |
| 7,514,007 B2 | 4/2009 | Chen et al. |
| 7,541,167 B2 | 6/2009 | Dave et al. |
| 7,547,747 B2 | 6/2009 | Hashimoto et al. |
| 7,553,658 B2 | 6/2009 | Kepka et al. |
| 7,625,764 B2 | 12/2009 | Stayton et al. |
| 7,632,656 B2 | 12/2009 | Kanazawa et al. |
| 7,695,905 B2 | 4/2010 | Furukawa et al. |
| 7,767,399 B2 | 8/2010 | Murphy et al. |
| 8,133,457 B2 | 3/2012 | Ribault et al. |
| 8,163,886 B2 | 4/2012 | Moya |
| 8,241,591 B2 | 8/2012 | Ribault et al. |
| 8,263,343 B2 | 9/2012 | Hallgren et al. |
| 8,362,217 B2 | 1/2013 | Moya et al. |
| 8,569,464 B2 | 10/2013 | Moya et al. |
| 8,691,918 B2 | 4/2014 | Jaber et al. |
| 8,915,374 B2 | 12/2014 | Franks et al. |
| 8,999,702 B2 | 4/2015 | Kelly, Jr. et al. |
| 9,090,930 B2 | 7/2015 | Ribault et al. |
| 9,174,860 B2 | 11/2015 | Franks et al. |
| 2002/0058786 A1 | 5/2002 | Chivers |
| 2002/0098567 A1 | 7/2002 | Vaidya et al. |
| 2003/0059840 A1 | 3/2003 | Chilkoti |
| 2003/0085228 A1 | 5/2003 | Oakes |
| 2003/0186293 A1 | 10/2003 | Ohnishi et al. |
| 2004/0009473 A1 | 1/2004 | Pease |
| 2004/0010163 A1 | 1/2004 | Hilbrig |
| 2004/0029143 A1 | 2/2004 | Van Ness et al. |
| 2004/0039177 A1 | 2/2004 | Yamanaka et al. |
| 2004/0058436 A1 | 3/2004 | Zhang et al. |
| 2004/0062140 A1 | 4/2004 | Cadogan et al. |
| 2004/0134846 A1 | 7/2004 | Akiyama et al. |
| 2004/0185437 A1 | 9/2004 | Hermet et al. |
| 2004/0219628 A1 | 11/2004 | Tashiro et al. |
| 2004/0248774 A1 | 12/2004 | Tayot |
| 2005/0016620 A1 | 1/2005 | Proulx et al. |
| 2005/0063259 A1 | 3/2005 | Isshiki et al. |
| 2005/0158782 A1 | 7/2005 | Furukawa et al. |
| 2005/0158851 A1 | 7/2005 | Furey et al. |
| 2005/0175702 A1 | 8/2005 | Muller-Schulte |
| 2005/0224415 A1 | 10/2005 | Akiyama et al. |
| 2005/0238620 A1 | 10/2005 | Gomer et al. |
| 2005/0272146 A1 | 12/2005 | Hodge et al. |
| 2005/0282169 A1 | 12/2005 | Turner et al. |
| 2006/0121519 A1 | 6/2006 | Patchornik |
| 2006/0162882 A1 | 7/2006 | O'Hara et al. |
| 2006/0189795 A1 | 8/2006 | Van Alstine et al. |
| 2006/0251610 A1 | 11/2006 | Nakahama |
| 2006/0257993 A1 | 11/2006 | McDevitt et al. |
| 2006/0270036 A1 | 11/2006 | Goodwin et al. |
| 2006/0281158 A1 | 12/2006 | Felder et al. |
| 2007/0148437 A1 | 6/2007 | Muller-Schulte |
| 2007/0193954 A1 | 8/2007 | Busson |
| 2007/0224241 A1 | 9/2007 | Stayton et al. |
| 2007/0249737 A1 | 10/2007 | Miller et al. |
| 2007/0298451 A1 | 12/2007 | Ribault et al. |
| 2008/0032396 A1 | 2/2008 | Chokshi |
| 2008/0131957 A1 | 6/2008 | Ryan et al. |

(56) References Cited

U.S. PATENT DOCUMENTS

| | | |
|---|---|---|
| 2008/0160559 A1 | 7/2008 | Carre et al. |
| 2008/0193981 A1 | 8/2008 | Fahrner et al. |
| 2008/0220531 A1 | 9/2008 | Stayton et al. |
| 2008/0255027 A1 | 10/2008 | Moya et al. |
| 2008/0284163 A1 | 11/2008 | Proulx et al. |
| 2008/0293118 A1 | 11/2008 | Furukawa et al. |
| 2008/0293926 A1 | 11/2008 | Hallgren et al. |
| 2009/0001025 A1 | 1/2009 | Takahashi et al. |
| 2009/0036651 A1 | 2/2009 | Moya |
| 2009/0050566 A1 | 2/2009 | Kozlov et al. |
| 2009/0130704 A1 | 5/2009 | Gyure |
| 2009/0148961 A1 | 6/2009 | Luchini et al. |
| 2009/0155201 A1 | 6/2009 | Mandeville, III et al. |
| 2009/0181450 A1 | 7/2009 | Ribault et al. |
| 2009/0232737 A1 | 9/2009 | Moya et al. |
| 2009/0233327 A1 | 9/2009 | Lau et al. |
| 2009/0311776 A1 | 12/2009 | Kelly, Jr. et al. |
| 2010/0012589 A1 | 1/2010 | Ribault et al. |
| 2010/0190963 A1 | 7/2010 | Moya et al. |
| 2010/0193148 A1 | 8/2010 | McKay et al. |
| 2010/0200507 A1 | 8/2010 | Kozlov et al. |
| 2010/0267933 A1 | 10/2010 | Wilson |
| 2010/0282425 A1 | 11/2010 | Karppi et al. |
| 2011/0020327 A1 | 1/2011 | Moya et al. |
| 2011/0065900 A1 | 3/2011 | Johansson et al. |
| 2011/0174735 A1 | 7/2011 | Ribault et al. |
| 2011/0257435 A1 | 10/2011 | Favero et al. |
| 2011/0313066 A1 | 12/2011 | Jaber et al. |
| 2012/0070836 A1 | 3/2012 | Zillmann et al. |
| 2012/0077249 A1 | 3/2012 | Ramaswamy et al. |
| 2012/0283419 A1 | 11/2012 | Thiyagarajan et al. |
| 2013/0005950 A1 | 1/2013 | Moya et al. |
| 2013/0123476 A1 | 5/2013 | Moya |
| 2013/0317204 A1 | 11/2013 | Moya et al. |
| 2014/0171594 A1 | 6/2014 | Jaber et al. |
| 2014/0263011 A1 | 9/2014 | Thiyagarajan et al. |
| 2015/0133636 A1 | 5/2015 | Xenopoulos et al. |
| 2015/0291656 A1 | 10/2015 | Hobel et al. |

FOREIGN PATENT DOCUMENTS

| | | |
|---|---|---|
| EP | 0420937 B1 | 11/1994 |
| EP | 0922715 A2 | 6/1999 |
| EP | 0851768 B1 | 4/2002 |
| EP | 1923461 A1 | 5/2008 |
| GB | 2297926 A | 8/1996 |
| GB | 2305936 A | 4/1997 |
| JP | 11-505714 A | 5/1999 |
| KR | 10-2009-0113264 A | 10/2009 |
| WO | 91/00360 A1 | 1/1991 |
| WO | 92/20373 A1 | 11/1992 |
| WO | 93/04173 A1 | 3/1993 |
| WO | 93/08829 A1 | 5/1993 |
| WO | 93/14110 A1 | 7/1993 |
| WO | 93/16185 A2 | 8/1993 |
| WO | 94/15951 A1 | 7/1994 |
| WO | 95/06249 A1 | 3/1995 |
| WO | 95/19181 A1 | 7/1995 |
| WO | 95/23865 A1 | 9/1995 |
| WO | 96/02577 A1 | 2/1996 |
| WO | 96/27011 A1 | 9/1996 |
| WO | 96/30046 A1 | 10/1996 |
| WO | 96/37600 A1 | 11/1996 |
| WO | 96/40210 A1 | 12/1996 |
| WO | 97/26912 A2 | 7/1997 |
| WO | 98/06248 A2 | 2/1998 |
| WO | 98/23761 A1 | 6/1998 |
| WO | 98/33162 A1 | 7/1998 |
| WO | 98/45331 A2 | 10/1998 |
| WO | 98/51793 A1 | 11/1998 |
| WO | 99/01556 A2 | 1/1999 |
| WO | 00/12618 A1 | 3/2000 |
| WO | 00/46262 A1 | 8/2000 |
| WO | 00/67901 A1 | 11/2000 |
| WO | 00/75348 A1 | 12/2000 |
| WO | 01/07548 A1 | 2/2001 |
| WO | 01/40309 A2 | 6/2001 |
| WO | 2004/056312 A2 | 7/2004 |
| WO | 2004/092393 A1 | 10/2004 |
| WO | 2005/010141 A2 | 2/2005 |
| WO | 2005/021129 A1 | 3/2005 |
| WO | 2005/108546 A1 | 11/2005 |
| WO | 2005/118771 A2 | 12/2005 |
| WO | 2006/085321 A2 | 8/2006 |
| WO | 2006/138143 A1 | 12/2006 |
| WO | 2007/002690 A2 | 1/2007 |
| WO | 2007/038523 A2 | 4/2007 |
| WO | 2007/073311 A1 | 6/2007 |
| WO | 2007/104456 A1 | 9/2007 |
| WO | 2007/148230 A2 | 12/2007 |
| WO | 2008/004988 A1 | 1/2008 |
| WO | 2008/079280 A1 | 7/2008 |
| WO | 2008/079302 A2 | 7/2008 |
| WO | 2008/091740 A2 | 7/2008 |
| WO | 2008/097154 A1 | 8/2008 |
| WO | 2009/089570 A1 | 7/2009 |
| WO | 2009/141664 A1 | 11/2009 |
| WO | 2009/158606 A2 | 12/2009 |
| WO | 2010/082894 A1 | 7/2010 |
| WO | 2014/123484 A1 | 8/2014 |
| WO | 2014/123485 A1 | 8/2014 |
| WO | 2014/133458 A1 | 9/2014 |
| WO | 2014/133459 A1 | 9/2014 |
| WO | 2014/133460 A1 | 9/2014 |

OTHER PUBLICATIONS

Kona, No. 20, 2002, pp. 246-250, "Flocculation Mechanism of Suspended Particles Using the Hydrophilic/Hydrophobic Transition of a Thermosensitive Polymer", Sakohara, et al.

Advanced Drug Delivery Reviews, vol. 58, No. 15, 2006, pp. 1655-1670, "Thermo-and pH-responsive polymers in drug delivery", Schmaljohann.

The Journal of Physical Chemistry B, vol. 111, No. 29, 2007, pp. 8649-8654, "Cationic Flocculants Carrying Hydrophobic Functionalities: Applications for Solid/Liquid Separation", Schwarz, et al.

Biotechnology and Bioengineering, vol. 34, No. 3, 1989, pp. 387-393, "Purification of Wheat Germ Agglutinin Using Affinity Flocculation with Chitosan and a Subsequent Centrifugation or Flotation Step", Senstad, et al.

Macromolecules, American Chemical Society, vol. 24, No. 15, 1991, pp. 4255-4263, "Self-organization of Poly(allylamine)s Containing Hydrophobic Groups and Its Effect on the Interaction with Small Molecules. 1. Static Fluorometry", Seo, et al.

J. Exp. Med., vol. 175, 1992, pp. 217-225, "Development of Humanized Bispecific Antibodies Reactive with Cytotoxic Lymphocytes and Tumor Cells Overexpressing the HER2 Protooncogene", Shalaby, et al.

Journal of Biotechnology, vol. 49, 1996, pp. 173-178, "Flocculation of cell, cell debris and soluble protein with methacryloyloxyethyl trimethylammonium chloride-acrylonitrile copolymer", Shan, et al.

Cancer Research (Suppl.), vol. 55, Dec. 1995, pp. 5935s-5945s, "Evaluation of a Complementarity-Determining Region-Grafted (Humanized) Anti-Carcinoembryonic Antigen Monoclonal Antibody in Preclinical and Clinical Studies", Sharkey, et al.

The Journal of Immunology, vol. 151, No. 4, 1993, pp. 2296-2308, "A Humanized CD18 Antibody Can Block Function Without Cell Destruction", Sims, et al.

Chest, vol. 103, No. 3, Mar. 1993, pp. 932-943, "Immunologic Therapy for ARDS, Septic Shock, and Multiple-Organ Failure", St. John, et al.

Cell, vol. 66, No. 6, 1991, pp. 1133-1144, "The B Lymphocyte Adhesion Molecule CD22 Interacts with Leukocyte Common Antigen CD45RO on T Cells and a2-6 Sialyltransferase, CD75, on B Cells", Stamenkovic, et al.

The Affinity Precipitation for the Isolation of Biomolecules, No. 3862, Aug. 2007, pp. 1-130, 146 pages, Stocker-majd, et al, submitted in two parts.

(56) References Cited

OTHER PUBLICATIONS

Transplant International, vol. 4, No. 1, 1991, pp. 3-7, "Anti-LFA1 monoclonal antibody (25.3) for treatment of steroid-resistant grade III-IV acute graft-versus-host disease", Stoppa, et al.

Journal of Chromatography A, vol. 1114, 2006, pp. 239-249, "Temperature sensitive dopamine-imprinted (N,N-methylene-bis-acrylamide cross-linked) polymer and its potential application to the selective extraction of adrenergic drugs from urine", Suedee, et al.

Analytical Sciences, vol. 3, No. 6, Dec. 1987, pp. 479-488, "Ion-Association Reagents, A Review", Toei.

The EMBO Journal, vol. 10, No. 12, 1991, pp. 3655-3659, "Bispecific single chain molecules (Janusins) target cytotoxic lymphocytes on HIV infected cells", Traunecker, et al.

The Journal of Immunology, vol. 147, No. 1, Jul. 1991, pp. 60-69, "Trispecific F(ab')3 derivatives that use cooperative signaling via the TCR/CD3 complex and CD2 to activate and redirect resting cytotoxic T cells", Tutt, et al.

Flocculation in Biotechnology and Separation Systems, 1987, pp. 351-368, "Aspects of Bioflocculation: An Overview", Unz.

Nature Biotechnology, vol. 14, 1996, pp. 309-314, "Human Antibodies with Sub-nanomolar Affinities Isolated from a Large Non-immunized Phage Display Library", Vaughan, et al.

Science, vol. 239, Mar. 1988, pp. 1534-1536, "Reshaping Human Antibodies: Grafting an Antilysozyme Activity", Verhoeyen, et al.

Nucleic Acids Research, vol. 21, No. 9, 1993, pp. 2265-2266, "Combinatorial infection and in vivo recombination: a strategy for making large phage antibody repertoires", Waterhouse, et al.

Biotechnology and Bioengineering, vol. 108, No. 1, Jan. 2011, pp. 50-58, "Effects of Solution Environment on Mammalian Cell Fermentation Broth Properties: Enhanced Impurity Removal and Clarification Performance", Westoby, et al.

Biotechnology and Bioengineering, vol. 86, No. 6, 2004, pp. 612-621, "Clearance of Minute Virus of Mice by Flocculation and Microfiltration", Wickramasinghe, et al.

Desalination, vol. 147, No. 1-3, 2002, pp. 25-30, "Enhanced microfiltration of yeast by flocculation", Wickramasinghe, et al.

Separation Science and Technology, vol. 37, No. 1, pp. 217-228, 2002, "Selective Precipitation of Water-Soluble Proteins Using Designed Polyelectrolyte", Yu, et al.

Protein Engineering, vol. 8, No. 10, 1995, pp. 1057-1062, "Engineering linear F(ab')2 fragments for efficient production in *Escherichia coli* and enhanced antiproliferative activity", Zapata, et al.

Nucleic Acids Research, vol. 31, No. 13, 2003, pp. 3406-3415, "Mfold web server for nucleic acid folding and hybridization prediction", Zuker.

International Search Report mailed Mar. 31, 2008 in corresponding PCT application No. PCT/US2007/26040.

International Search Report dated Apr. 24, 2008 in corresponding PCT application No. PCT/US2007/26090.

International Search Report dated Aug. 27, 2009 in corresponding PCT application No. PCT/US2008/013736.

International Search Report dated Feb. 8, 2010 in co-pending PCT application No. PCT/US2009/006363.

International Search Report/Written Opinion dated Dec. 6, 2011 in co-pending PCT application No. PCT/US2011/039595.

International Search Report dated Oct. 31, 2011 in co-pending PCT application No. PCT/US2011/036648.

Office Action mailed Jun. 21, 2011 in co-pending U.S. Appl. No. 12/316,708.

Office Action mailed Feb. 29, 2012 in corresponding U.S. Appl. No. 12/316,708.

Final Rejection mailed Sep. 25, 2012 in corresponding U.S. Appl. No. 12/316,708.

Office Action-Restriction-mailed Feb. 7, 2012 in corresponding U.S. Appl. No. 12/448,004.

Office Action mailed Jul. 26, 2012 in corresponding U.S. Appl. No. 12/448,004.

Office Action-Restriction-mailed Apr. 27, 2012 in co-pending U.S. Appl. No. 12/592,744.

Office Action Feb. 21, 2012 in co-pending U.S. Appl. No. 12/387,688.

Office Action-Restriction-mailed Jul. 17, 2012 in co-pending U.S. Appl. No. 12/633,141.

Office Action mailed Jan. 31, 2013 in co-pending U.S. Appl. No. 12/633,141.

Office Action mailed Feb. 22, 2013 in co-pending U.S. Appl. No. 13/610,954.

Office Action mailed Mar. 15, 2013 in co-pending U.S. Appl. No. 13/108,576.

Final Rejection mailed Dec. 28, 2012 in co-pending U.S. Appl. No. 12/387,688.

Office Action-Restriction-mailed Nov. 21, 2012 in co-pending U.S. Appl. No. 13/155,912.

Journal of Molecular Biology, vol. 227, No. 2, Sep. 1992, pp. 381-388, "By-passing Immunisation: Human Antibodies from Synthetic Repertoires of Germline VH Gene Segments Rearranged in vitro", Hoogenboom, et al.

Molecular Immunology, vol. 28, No. 9, Sep. 1991, pp. 1027-1037, "Construction and expression of antibody-tumor necrosis factor fusion proteins", Hoogenboom, et al.

Biotechnology and Bioengineering, vol. 60, No. 5, Dec. 1998, pp. 568-579, "Preparation of a New Thermo-Responsive Adsorbent with Maltose as a Ligand and Its Application to Affinity Precipitation", Hoshino, et al.

Transplantation, vol. 58, No. 3, 1994, pp. 377-380, "Administration of an anti-CD11a monoclonal antibody in recipients of kidney transplantation. A pilot study", Hourmant, et al.

Biotechnology Techniques, vol. 4, No. 1, 1990, pp. 55-60, "The Flocculation of Bacteria Using Cationic Synthetic Flocculants and Chitosan", Hughes, et al.

Bioseparation, vol. 7, No. 4-5, 1999, pp. 207-220, "Polycomplexes—potential for bioseparation", Izumrudov, et al.

Proc. Natl. Acad. Sci. USA, vol. 90, Mar. 1993, pp. 2551-2555, "Analysis of homozygous mutant chimeric mice: Deletion of the immunoglobulin heavy-chain joining region blocks B-cell development and antibody production", Jakobovits, et al.

Nature, vol. 362, Mar. 1993, pp. 255-258, "Germ-line transmission and expression of a human-derived yeast artificial chromosome", Jakobovits, et al.

Nature, vol. 321, May 1986, pp. 522-525, "Replacing the complementarity-determining regions in a human antibody with those from a mouse", Jones, et al.

Cancer Research (Suppl.), vol. 55, Dec. 1995, pp. 5908s-5910s, "Radiolabeled Anti-CD33 Monoclonal Antibody M195 for Myeloid Leukemias", Jurcic, et al.

Cancer Research (Suppl.), vol. 55, Dec. 1995, pp. 5899s-5907s, "Treatment of Non-Hodgkin's Lymphoma with Radiolabeled Murine, Chimeric, or Humanized LL2, an Anti-CD22 Monoclonal Antibody", Juweid, et al.

Biotechnology and Bioengineering, vol. 40, No. 11, Dec. 1992, pp. 1381-1387, "Purification of Recombinant Protein A by Aqueous Two-Phase Extraction Integrated with Affinity Precipitation", Kamihira, et al.

Anal. Chem., vol. 69, No. 5, 1997, pp. 823-830, "Temperature-Responsive Liquid Chromatography. 2. Effects of Hydrophobic Groups in N-isopropylacrylamide Copolymer-modified Silica", Kanazawa, et al.

Journal of Chromatography A, vol. 1106, Feb. 2006, pp. 152-158, "Temperature-responsive stationary phase utilizing a polymer of proline derivative for hydrophobic interaction chromatography using an aqueous mobile phase", Kanazawa, et al.

Biochemical Engineering Journal, vol. 40, No. 3, 2008, pp. 512-519, "Flocculation enhanced microfiltration of *Escherichia coli* lysate", Karim, et al.

Journal of Membrane Science, vol. 182, No. 1-2, Feb. 2001, pp. 161-172, "Flocculation to enhance microfiltration", Kim, et al.

Flocculation in Biotechnology and Separation Systems, 1987, pp. 429-439, "Removal of Cell and Cell Debris by Electrostatic Adsorption of Positively Charged Polymeric Particles", Kim, et al.

Growth Factors, vol. 7, 1992, pp. 53-64, "The Vascular Endothelial Growth Factor Proteins: Identification of Biologically Relevant Regions by Neutralizing Monoclonal Antibodies", Kim, et al.

(56) References Cited

OTHER PUBLICATIONS

The Journal of Immunology, pp. 2453-2455, Reprinted with permission from Nature, vol. 256 (5517): 495-497 (1975), "Continuous cultures of fused cells secreting antibody of predefined specificity", Kohler, et al.
The Journal of Immunology, vol. 148, No. 5, 1992, pp. 1547-1553, "Formation of a bispecific antibody by the use of leucine zippers", Kostelny, et al.
The Journal of Immunology, vol. 133, No. 6, 1984, pp. 3001-3005, "A human hybrid myeloma for production of human monoclonal antibodies", Kozbor, et al.
Isolation and Purification of Proteins, 2003, edited by Rajni Hatti-Kaul, et al., pp. 237-275, "Precipitation of Proteins", Kumar, et al.
Biotechnology and Bioengineering, vol. 59, Issue 6, 1998, pp. 695-704, "Affinity Precipitation of Amylase Inhibitor from Wheat Meal by Metal Chelate Affinity Binding Using Cu(II)-Loaded Copolymers of 1-Vinylimidazole with N-Isopropylacrylamide", Kumar, et al.
Prog. Polym. Sci., vol. 32, 2007, pp. 1205-1237, "Smart polymers: Physical forms and bioengineering applications", Kumar, et al.
Biotechnology and Bioengineering, vol. 75, No. 5, Dec. 2001, pp. 570-580, "Type-Specific Separation of Animal Cells in Aqueous Two-Phase Systems Using Antibody Conjugates with Temperature-Sensitive Polymers", Kumar, et al.
Am Chem Society, ACS Symposium Series, vol. 362, Chapter 7, 1988, pp. 72-101, "Scale-Up of Bioseparations for Microbial and Biochemical Technology", Ladisch, et al.
Nature, vol. 227, No. 5259, Aug. 1970, pp. 680-685, "Cleavage of Structural Proteins during the Assembly of the Head of Bacteriophage T4", Laemmli.
Bioseparation, vol. 7, 1999, pp. 195-205, "Carboxymethyl cellulose as a new heterobifunctional ligand carrier for affinity precipitation of proteins", Lali, et al.
Journal of Biotechnology, vol. 49, No. 1-3, Aug. 1996, pp. 189-199, "Evaluation of affinity precipitation and a traditional affinity chromatographic precedure for purification of soybean lectin, from extracts of soya flour", Larsson, et al.
Journal of Pharmaceutical Sciences, vol. 100, No. 7, Jul. 2011, pp. 2551-2562, "Assessment of Net Charge and Protein-Protein Interactions of Different Monoclonal Antibodies", Lehermayr, et al.
AIChE Journal, vol. 55, No. 8, Aug. 2009, pp. 2070-2080, "Effect of Molecular Weight of Poly(N-isopropylacrylamide) Temperature-Sensitive Flocculants on Dewatering", Li, et al.
European Journal of Immunology, vol. 26, No. 1, Jan. 1996, pp. 1-9, "Antibody-targeted superantigen therapy induces tumor-infiltrating lymphocytes, excessive cytokine production, and apoptosis in human colon carcinoma", Litton, et al.
The Journal of Immunology, vol. 156, No. 4, 1996, pp. 1646-1653, "In Vivo Blockade of TNF-alpha by Intravenous Infusion of a Chimeric Monoclonal TNF-alpha Antibody in Patients with Rheumatoid Arthritis. Short Term Cellular and Molecular Effects", Lorenz, et al.
Journal of Chromatography B, vol. 878, No. 9-10, Mar. 2010, pp. 798-806, "Using precipitation by polyamines as an alternative to chromatographic separation in antibody purification processes", Ma, et al.
Innovative Food Science and Emerging Technologies, 2007, pp. 1-11, "Novel chromatographic separation—The potential of smart polymers", Maharjan, et al.
Analytical Chemistry, vol. 75, No. 13, Jul. 2003, pp. 2943-2949, "A Smart Microfluidic Affinity Chromatography Matrix Composed of Poly(N-isopropylacrylamide)-Coated Beads", Malmstadt, et al.
Bioconjugate Chem., 2003, vol. 14, No. 3, pp. 575-580, "Affinity Thermoprecipitation and Recovery of Biotinylated Biomolecules via a Mutant Streptavidin-Smart Polymer Conjugate", Malmstadt, et al.
Journal of Molecular Biology, vol. 222,, No. 3, Dec. 1991, pp. 581-597, "By-passing Immunization—Human Antibodies from V-gene Libraries Displayed on Phage", Marks, et al.
Bio/Technology, Nature Publishing Group, vol. 10, Jul. 1992, pp. 779-783, "By-Passing Immunization: Building High Affinity Human Antibodies by Chain Shuffling", Marks, et al.

Nature, vol. 348, Dec. 1990, pp. 552-554, "Phage antibodies: filamentous phage displaying antibody variable domains", McCafferty, et al.
Millipore Pure Science Laboratory Catalogue 1999/2000, Ultrafiltration Discs and Stirred Cells, p. 127, "Solvent-resistant Stirred Cells" and "High-Output Stirred Cells", 3 pages.
Nature, vol. 305, Oct. 1983, pp. 537-540, "Hybrid hybridomas and their use in immunohistochemistry", Milstein, et al.
Journal of Biochemical and Biophysical Methods, vol. 24, 1992, pp. 107-117, "Single-step purification of F(ab')sub.2 fragments of mouse monoclonal antibodies (immunoglobulins G1) by hydrophobic interaction high performance liquid chromatography using TSKgel Phenyl-5PW", Morimoto, et al.
Proc. Natl. Acad. Sci. USA, vol. 81, Nov. 1984, pp. 6851-6855, "Chimeric human antibody molecules: Mouse antigen-binding domains with human constant region domains", Morrison, et al.
American Inst. of Chem. Engineers, Biotechnology Progress, V 26, No. 5, (2010), pp. 1322-1331, "Monoclonal Antibody Purification Using Cationic Polyelectrolytes: An Alternative to Column Chromatography", Peram, et al.
Flocculation in Biotechnology and Separation Systems, 1987, pp. 457-466, "Flocculation of Cell Debris for Improved Separation by Centrifugation", Persson, et al.
The Journal of Immunology, vol. 151, No. 5, Sep. 1993, pp. 2623-2632, "Humanization of an Antibody Directed Against IgE", Presta, et al.
Current Opinion in Structural Biology, vol. 2, No. 4, Aug. 1992, pp. 593-596, "Antibody Engineering", Presta.
Cancer Research (Suppl.), vol. 55, Dec. 1995, pp. 5916s-5920s, "Radioimmunotherapy for Breast Cancer Using Escalating Fractionated Doses of 131-I-labeled Chimeric L6 Antibody with Peripheral Blood Progenitor Cell Transfusions", Richman, et al.
Nature, vol. 332, Mar. 1988, pp. 323-327, "Reshaping human antibodies for therapy", Riechmann, et al.
International Search Report and Written opinion dated Jan. 29, 2010 in co-pending PCT application No. PCT/US2009/67097, 8 pages.
International Preliminary Report on Patentability mailed Jun. 30, 2011 in co-pending PCT Patent Application No. PCT/US2009/067097, 7 pages.
Extended European Search Report mailed Nov. 17, 2009 in co-pending EP Patent Application No. 09161982.5, 6 pages.
International Search Report/Written Opinion mailed Nov. 12, 2009 in co-pending PCT Patent Application No. PCT/US2009/002787, 9 pages.
International Preliminary Report on Patentability issued Dec. 13, 2010 in co-pending PCT Patent Application No. PCT/US2009/002787, 6 pages.
Office Action dated Nov. 17, 2010 in co-pending U.S. Appl. No. 12/387,688.
Final Rejection dated Apr. 21, 2011 in co-pending U.S. Appl. No. 12/387,688.
Merriam Webster Dictionary, accessed May 14, 2010 at http://www.merriam-webster.com/dictionary/associated, Definition of the word "associate . . . " 6 pages.
Office Action mailed Apr. 15, 2013 in co-pending U.S. Appl. No. 13/108,576.
Office Action mailed Apr. 30, 2013 in co-pending U.S. Appl. No. 13/155,912.
International Preliminary Report on Patentability mailed Jun. 30, 2011 in co-pending PCT application No. PCT/US2009/006363.
International Preliminary Report on Patentability mailed Nov. 29, 2012 in co-pending PCT application No. PCT/US2011/036648.
International Preliminary Report on Patentability mailed Dec. 20, 2012 in co-pending PCT application No. PCT/US2011/039595.
Final Rejection mailed Jun. 25, 2013 in co-pending U.S. Appl. No. 12/633,141.
Notice of Allowance mailed Aug. 21, 2013 in corresponding U.S. Appl. No. 12/316,708.
Final Rejection mailed Aug. 19, 2013 in co-pending U.S. Appl. No. 12/387,688.
Office Action—Restriction—mailed Oct. 28, 2013 in corresponding U.S. Appl. No. 13/955,024.

(56) References Cited

OTHER PUBLICATIONS

Notice of Allowance mailed Oct. 31, 2013 in co-pending U.S. Appl. No. 13/610,954.
Final Rejection mailed Oct. 22, 2013 in co-pending U.S. Appl. No. 13/108,576.
Protein Expression and Purification, vol. 7, Article No. 0042, 1996, pp. 294-298, "Sequential Precipitation with Reversibly Soluble Insoluble Polymers as a Bioseparation Strategy: Purification of B-Glucosidase from Trichoderma longibrachiatum", Agarwal, et al.
Journal of Chromatography B, vol. 761, No. 2, 2001, pp. 247-254, "New antibody purification procedure using a thermally responsive poly(N-isopropylacrylamide)-dextran derivative conjugate", Anastase-Ravion, et al.
Cell, vol. 61, No. 7, Jun. 1990, pp. 1303-1313, "CD44 is the Principal Cell Surface Receptor for Hyaluronate", Aruffo, et al.
Process Technology Proceedings, vol. 4, Proceedings of the International Symposium on Flocculation in Biotechnology and Separations Systems, San Francisco, California, Jul. 28-Aug. 1, 1986, pp. 429 & 441, "Flocculation in Biotechnology and Separation Systems", Attia.
Journal of Chromatography A, vol. 1119, 2006, pp. 58-65, "Aqueous chromatography system using pH- and temperature-responsive stationary phase with ion-exchange groups", Ayano, et al.
Science, vol. 229, Jul. 1985, pp. 81-83, "Preparation of Bispecific Antibodies by Chemical Recombination of Monoclonal Immunoglobulin G1 Fragments", Brennan, et al.
Monoclonal Antibody Production Techniques and Application, pp. 51-63 (Marcel Dekker, Inc., New York 1987), "Mouse-Human Myeloma Partners for the Production of Heterohybridomas", Brodeur, et al.
The Year in Immunology, vol. 7, 1993, pp. 33-40, "Designer Mice: The Production of Human Antibody Repertoires in Transgenic Animals", Bruggemann, et al.
Bio/Technology, Nature Publishing Group, vol. 10, Feb. 1992, pp. 163-167, "High Level *Escherichia coli* Expression and Production of a Bivalent Humanized Antibody Fragment", Carter, et al.
Macromolecular Bioscience, vol. 5, No. 5, 2005, pp. 373-378, "Highly Branched Stimuli Responsive Poly[(N-isopropylacrylamide)-co-(1,2-propandiol-3-methacrylate)]s with Protein Binding Functionality", Carter, et al.
Proc. Natl. Acad. Sci. USA, vol. 89, May 1992, pp. 4285-4289, "Humanization of an anti-p185HER2 antibody for human cancer therapy", Carter, et al.
"Technology: Temperature-responsive polymers", document retrieved on Oct. 13, 2010, available at: http://www.cellseed.com/technology-e/index.html, 1 page, Cellseed, Inc.
Cancer Research (Suppl.), vol. 55, Dec. 1, 1995, pp. 5852s-5856s, "Biological Activity of Two Humanized Antibodies against Two Different Breast Cancer Antigens and Comparison to Their Original Murine Forms", Ceriani, et al.
Macromolecular Chemistry and Physics, vol. 196, No. 4, Apr. 1995, pp. 1251-1259, "A new temperature- and pH-responsive copolymer for possible use in protein conjugation", Chen, et al.
Nature, vol. 373, No. 5, Jan. 1995, pp. 49-52, "Graft copolymers that exhibit temperature-induced phase transitions over a wide range of pH", Chen, et al.
Langmuir, vol. 21, No. 25, 2005, pp. 11673-11677, "pH-Dependence of the Properties of Hydrophobically Modified Polyvinylamine", Chen, et al.
Biomaterials, vol. 11, No. 9, Nov. 1990, pp. 631-633, "Polymer-protein conjugates. II. Affinity precipitation separation of human immunogammaglobulin by a poly (N-isopropylacrylamide)-protein A conjugate", Chen, et al.
Colloids and Surfaces B: Biointerfaces, vol. 6, 1996, pp. 37-49, "Characterization of pH-sensitive polymeric supports for selective precipitation of proteins", Chern, et al.
Journal of Molecular Biology, vol. 196, 1987, pp. 901-917, "Canonical Structures for the Hypervariable Regions of Immunoglobulins", Chothia, et al.
Arthritis & Rheumatism, vol. 39, No. 1, Jan. 1996, pp. 52-56, "Percentage of anti-CD4 monoclonal antibody-coated lymphocytes in the rheumatoid joint is associated with clinical improvement. Implications for the development of immunotherapeutic dosing regimens", Choy, et al.
Nature, vol. 352, Aug. 1991, pp. 624-628, "Making antibody fragments using phage display libraries", Clackson, et al.
Bioseparation, vol. 7, No. 4-5, Jul. 1999, pp. 231-240, "Affinity precipitation of monoclonal antibodies by nonstoichiometric polyelelectrolyte complexes", Dainiak, et al.
Journal of Colloid and Interface Science, vol. 179, No. 1, 1996, pp. 188-193, "Temperature-Sensitive Flocculants Based on Poly (N-isopropylacrylamide-co-diallyldimethylammonium Chloride)", Deng, et al.
Critical Care Medicine, vol. 23, No. 9, Sep. 1995, pp. 1461-1469, "CDP571, a humanized antibody to human tumor necrosis factor-alpha: Safety, pharmacokinetics, immune response, and influence of the antibody on cytokine concentrations in patients with septic shock", Dhainaut, et al.
Nature, vol. 411, May 2001, pp. 59-62, "Size-dependent control of the binding of biotinylated proteins to streptavidin using a polymer shield", Ding, et al.
Nature, vol. 355, Jan. 1992, pp. 258-262, "Immunization of hu-PBL-SCID mice and the rescue of human monoclonal Fab fragments through combinatorial libraries", Duchosal, et al.
Journal of Polymer Science, vol. XIII, No. 6, Feb. 1954, pp. 85-91, "Viscosities of Dilute Aqueous Solutions of a Partially Quaternized Poly-4-vinylpyridine at Low Gradients of Flow", Eisenberg, et al.
The Journal of Immunology, vol. 155, No. 2, 1995, pp. 925-937, "Engineered Anti-CD38 Monoclonal Antibodies for Immunotherapy of Multiple Myeloma", Ellis, et al.
Flocculation in Biotechnology and Separation Systems, 1987, pp. 441-455, "Flocculation of *E. Coli* Bacteria With Cationic Polyelectrolytes", Eriksson, et al.
Flocculation in Biotechnology and Separation Systems, 1987, pp. 383-398, "Genetic Control of Flocculation of Yeast With Respect to Application in Biotechnology", Esser, et al.
Journal of Chromatography A, vol. 1195, 2008, pp. 94-100, "Purification of human immunoglobulin G by thermoseparating aqueous two-phase systems", Ferriera, et al.
Biotechnology and Bioengineering, vol. 79, No. 3, Aug. 5, 2002, pp. 271-276, "Affinity Separation Using an Fv Antibody Fragment—"Smart" Polymer Conjugate", Fong, et al.
Bioconjugate Chem., vol. 10, No. 5, 1999, pp. 720-725, "Thermoprecipitation of Streptavidin via Oligonucleotide-Mediated Self-Assembly with Poly (N-isopropylacrylamide)", Fong, et al.
Chimia 55, No. 3, 2001, pp. 196-200, "Stimulus-Responsive Polymers for Bioseparation", Freitag, et al.
Trends in Biotechnology, vol. 9, No. 6, Jun. 1991, pp. 191-196, "Application of reversibly soluble polymers in bioprocessing", Fujii, et al.
Trends in Biotechnology, vol. 17, No. 8, Aug. 1999, pp. 335-340, "'Smart' polymers and what they could do in biotechnology and medicine", Galaev, et al.
Russian Chemical Reviews, vol. 64, No. 5, 1995, pp. 471-489, "'Smart' polymers in biotechnology and medicine", Galaev.
Journal of Chromatography A, vol. 684, 1994, pp. 45-54, "Interaction of Cibacron Blue with polymers: implications for polymer-shielded dye-affinity chromatography of phosphofructokinase from baker's yeast", Galaev, et al.
Biotechnology and Bioengineering, vol. 71, No. 3, 2000/2001, pp. 223-234, "Use of the Avidin (Imino)biotin System as a General Approach to Affinity Precipitation", Garret-Flaudy, et al.
Process Biochemistry, vol. 34, No. 6-7, Sep. 1999, pp. 577-580, "Purification of Aspergillus sp xylanase by precipitation with an anionic polymer Eudragit S 100", Gawande, et al.
Progress in Polymer Science, vol. 29, No. 12, Dec. 2004, pp. 1173-1222, "Stimuli-responsive polymers and their bioconjugates", Gil, et al.
Monoclonal Antibodies: Principles and Practice, Academic Press, 1986, pp. 59-103, "3. Production of Monoclonal Antibodies", Goding.

(56) References Cited

OTHER PUBLICATIONS

The Journal of Immunology, vol. 155, No. 10, 1995, pp. 4996-5002, "Construction and Characterization of a Humanized Anti-gamma-Ig Receptor Type I (Fc gamma RI) Monoclonal Antibody", Graziano, et al.
The Journal of Immunology, vol. 152, No. 11, 1994, pp. 5368-5374, "Efficient Tumor Cell Lysis Mediated by a Bispecific Single Chain Antibody Expressed in *Escherichia coli*", Gruber, et al.
Bioseparation, vol. 5, 1995, pp. 339-350, "Alternative modes of precipitation of Eudragit S-100: a potential ligand carrier for affinity precipitation of protein", Guoqiang, et al.
Journal of Molecular Recognition, vol. 9, 1996, pp. 356-359, XP-002538983, "Affinity Precipitation of Proteins", Gupta, et al.
Am Inst. of Chem Engineers Journal, Jul. 2003, vol. 49, No. 7, pp. 1687-1701, "Flocculation of Biological Cells: Experiment vs. Theory", Han, et al.
Analyst, vol. 129, 2004, pp. 421-427, "Capturing of acidic macromolecules from biological samples using a temperature-responsive polymer modified with poly-L-lysine", Hayashi, et al.
Journal of Chromatography B, vol. 790, Jun. 2003, pp. 79-90, "Protein purification by affinity precipitation", Hilbrig, et al.
The Proceedings of the National Academy of Sciences, USA, vol. 90, No. 14, Jul. 1993, pp. 6444-6448, "'Diabodies': Small bivalent and bispecific antibody fragments", Holliger, et al.
Final Rejection mailed Jun. 23, 2014 in co-pending U.S. Appl. No. 12/383,131.
Journal of the Chemical Society of Japan, No. 8, Aug. 1991, pp. 1115-1126 (English Abstract Submitted), "Structure and Hydrolysis Activity of Poly(alylamine)s having Hydrophobic Groups", SEO, et al.
European Search Report mailed Jul. 9, 2013 in co-pending European Patent Application No. EP 09835506.8.
Office Action mailed Dec. 9, 2013 in corresponding U.S. Appl. No. 13/955,024.
Notice of Allowance mailed Nov. 22, 2013 in co-pending U.S. Appl. No. 13/108,576.
French Search Report dated Jun. 2, 2009 in co-pending French patent application No. FA 713810/FR 0854844.
Office Action mailed Feb. 26, 2009 in co-pending U.S. Appl. No. 11/805,539.
Office Action mailed May 26, 2009 in co-pending U.S. Appl. No. 11/805,539.
Office Action mailed Jul. 30, 2009 in co-pending U.S. Appl. No. 11/805,539.
Final Rejection mailed Dec. 29, 2009 in co-pending U.S. Appl. No. 11/805,539.
Final Rejection mailed Apr. 20, 2010 in co-pending U.S. Appl. No. 11/805,539.
Final Rejection mailed Aug. 27, 2010 in co-pending U.S. Appl. No. 11/805,539.
Final Rejection mailed Jan. 7, 2011 in co-pending U.S. Appl. No. 11/805,539.
Office Action mailed Apr. 21, 2011 in co-pending U.S. Appl. No. 11/805,539.
Final Rejection mailed Oct. 18, 2011 in co-pending U.S. Appl. No. 11/805,539.
Advisory Action mailed Nov. 25, 2011 in co-pending U.S. Appl. No. 11/805,539.
Examiner's Answer to Appeal Brief mailed Jul. 3, 2012 in co-pending U.S. Appl. No. 11/805,539.
Office Action mailed Nov. 1, 2011 in co-pending U.S. Appl. No. 12/383,131.
Final Rejection mailed Apr. 13, 2012 in co-pending U.S. Appl. No. 12/383,131.
Office Action mailed Jun. 11, 2013 in co-pending U.S. Appl. No. 12/383,131.
Final Rejection mailed Oct. 24, 2013 in co-pending U.S. Appl. No. 12/383,131.
Office Action mailed Feb. 4, 2014 in co-pending U.S. Appl. No. 12/383,131.
Office Action mailed Feb. 27, 2014 in co-pending U.S. Appl. No. 12/387,688.
Office Action mailed Apr. 3, 2014 in co-pending U.S. Appl. No. 12/633,141.
Office Action mailed Dec. 19, 2014 in co-pending U.S. Appl. No. 12/383,131.
Office Action mailed Mar. 16, 2015 in corresponding U.S. Appl. No. 13/732,613.
Office Action mailed Mar. 2, 2015 in co-pending U.S. Appl. No. 12/633,141.
Notice of Allowance mailed Feb. 20, 2015 in co-pending U.S. Appl. No. 12/387,688.
Notice of Allowance mailed Jun. 4, 2015 in co-pending U.S. Appl. No. 12/383,131.
Final Rejection mailed Jul. 27, 2015 in co-pending U.S. Appl. No. 12/633,141.
Japanese communication, with English translation, dispatched Sep. 2, 2014 in co-pending Japanese patent application No. 2013-083213.
Office Action-Restriction—mailed Sep. 30, 2014 in corresponding U.S. Appl. No. 13/732,613.
Notice of Allowance mailed Aug. 4, 2014 in corresponding U.S. Appl. No. 13/955,024.
Office Action mailed Jul. 29, 2014 in co-pending U.S. Appl. No. 12/387,688.
Final Rejection mailed Aug. 14, 2014 in co-pending U.S. Appl. No. 12/633,141.
Notice of Allowance mailed Nov. 14, 2014 in co-pending U.S. Appl. No. 13/610,954.
Final rejection mailed Oct. 20, 2015 in co-pending U.S. Appl. No. 13/732,613.
Notice of Allowance mailed Sep. 4, 2015 in co-pending U.S. Appl. No. 13/955,024.
Notice of Allowance mailed Nov. 6, 2015 in co-pending U.S. Appl. No. 13/955,024.
Notice of Allowance mailed Oct. 20, 2015 in co-pending U.S. Appl. No. 13/610,954.
Notice of Allowance mailed Feb. 10, 2016 in co-pending U.S. Appl. No. 11/805,539.
Final rejection mailed Feb. 25, 2016 in co-pending U.S. Appl. No. 12/633,141.

* cited by examiner

PURIFICATION OF PROTEINS

This application is a continuation of U.S. patent application Ser. No. 12/004,319 filed Dec. 20, 2007, which claims priority of U.S. Provisional Application Ser. No. 60/876,330 filed Dec. 21, 2006, the disclosures of which are incorporated herein by reference.

The present invention relates to the purification of biomolecules. More particularly, it relates to the purification of biomolecules such as proteins, polypeptides, antibodies and the like, by a stimuli responsive polymer, such as a solubilized or soluble polymer to capture the desired biomolecules from a solution/suspension by a precipitation mechanism and then to further purify it.

BACKGROUND OF THE INVENTION

The general process for the manufacture of biomolecules, such as proteins, particularly recombinant proteins typically involves two main steps: (1) the expression of the protein in a host cell, followed by (2) the purification of the protein. The first step involves growing the desired host cell in a bioreactor to effect the expression of the protein, Some examples of cell lines used for this purpose include Chinese hamster ovary (CHO) cells, myeloma (NSO) bacterial cells such as *e-coli* and insect cells. Once the protein is expressed at the desired levels, the protein is removed from the host cell and harvested. Suspended particulates, such as cells, cell fragments, lipids and other insoluble matter are typically removed from the protein-containing fluid by filtration or centrifugation, resulting in a clarified fluid containing the protein of interest in solution as well as other soluble impurities.

The second step involves the purification of the harvested protein to remove impurities which are inherent to the process. Examples of impurities include host cell proteins (HCP, proteins other than the desired or targeted protein), nucleic acids, endotoxins, viruses, protein variants and protein aggregates.

This purification typically involves several chromatography steps, which can include affinity, ion exchange hydrophobic interaction, etc on solid matrices such as porous agarose, polymeric or glass.

One example of chromatography process train for the purification of proteins involves protein-A affinity, followed by cation exchange, followed by anion exchange. The protein-A column captures the protein of interest or target protein by an affinity mechanism while the bulk of the impurities pass through the column to be discarded. The protein then is recovered by elution from the column. Since most of the proteins of interest have isoelectric points (PI) in the basic range (8-9) and therefore being positively charged under normal processing conditions (pH below the PI of the protein), they are bound to the cation exchange resin in the second column. Other positively charged impurities are also bound to this resin. The protein of interest is then recovered by elution from this column under conditions (pH, salt concentration) in which the protein elutes while the impurities remain bound to the resin. The anion exchange column is typically operated in a flow through mode, such that any negatively charged impurities are bound to the resin while the positively charged protein of interest is recovered in the flow through stream. This process results in a highly purified and concentrated protein solution.

Other alternative methods for purifying proteins have been investigated in recent years, one such method involves a flocculation technique. In this technique, a soluble polyelectrolyte is added to a clarified or unclarified cell culture broth to capture the impurities thereby forming a flocculant, which is allowed to settle and can be subsequently removed from the protein solution.

The main drawback of this flocculation technique is that it requires that the polyelectrolyte be added in the exact amount needed to remove the impurities. If too little flocculent is added, impurities will remain in the protein solution and if too much flocculent is added, the excess polyelectrolyte needs to be removed from the resulting solution. The exact level of impurities in the broth is extremely difficult to predict due to the relatively large degree of variability in the process (from batch to batch) as well as the vast differences between processes to produce different proteins. Removing any excess polyelectrolyte is practically impossible because it is a soluble material and thus it is carried through the process as an undesirable impurity.

In co-pending application U.S. Ser. No. 60/876,330 filed Dec. 21, 2006, a polymer, soluble under certain conditions, such as temperature or pH, is used to bind impurities while in its soluble state and is then precipitated out upon a change in condition (pH or temperature, etc) removing the impurities with it. The biomolecule of interest is then further treated using traditional chromatography or membrane adsorbers and the like.

What is needed is a better process for purifying biomolecules.

SUMMARY OF THE INVENTION

The present invention relates to a stimuli responsive polymer such as a selectively soluble polymer capable of selectively and reversibly binding to one or more desired biomolecules in a biological material containing stream and the methods of using such a material to purify one or more desired biomolecules from such a stream.

The polymer is soluble under a certain set of process conditions such as pH, salt concentration or temperature and is rendered insoluble and precipitates out of solution upon a change in conditions (temperature, salt concentration or pH), e.g. a stimuli responsive polymer. Only when precipitated out of solution, the polymer is capable of binding to one or more desired biomolecules within the stream (protein, polypeptide, etc) in a cell broth using a ligand or functional group on the polymer. The precipitate can then be removed from the stream, such as by being filtered out from the remainder of the stream and the desired biomolecule is recovered such as by elution.

The insoluble polymer, bound to the desired biomolecule, can be washed one or more times to ensure that any impurities in the liquid or entrapped in or on the polymer have been removed and then the biomolecule of interest can be recovered, such as by being eluted from the polymer and recovered for further use or processing.

It is an object of the present invention to provide a stimuli responsive polymer to be soluble in a given condition and to become insoluble and form a precipitate in response to a change in condition.

It is an object of the present invention to provide a polymer that is capable of being selectively solubilized in a liquid under certain conditions and to be insoluble and to precipitate out of solution under different conditions in that liquid.

It is another object of the present invention to provide a polymer that is capable of being selectively solubilized in a liquid under certain conditions and to be insoluble and to precipitate out of solution under different conditions in that liquid and to allow for an overage of the polymer in solution and being able to recover substantially all the polymer from solution by precipitation.

It is a further object of the present invention to provide a polymer that is capable of being solubilized under a first certain set of conditions in the liquid and to be capable of binding to one or more entities in the liquid after being precipitated from the liquid under different conditions.

It is another object of the present invention to provide a polymer capable of being solubilized under certain ranges of pH, temperature, salt, temperature and salt concentration or the like and to have it bind to one or more desired biomolecules either during or after being precipitated under a different set of ranges of pH, temperature, salt, temperature and salt concentration or the like.

It is an object to use one or more polymers such as poly(N-vinyl caprolactam), poly(N-acryloylpiperidine), poly(N-vinylisobutyramide), poly (N-substituted acrylamide) including [poly(N-isopropylacrylamide), poly(N,N'-diethylacrylamide), and poly(N-acryloyl-N'-alkylpiperazine)], Hydroxyalkylcellulose, copolymers of acrylic acid and methacrylic acid, polymers and copolymers of 2 or 4-vinylpyridine and chitosan with either a ligand or functional group attached to it to selectively capture and reversibly bind to a desired biomolecule in order to purify the biomolecule from a stream containing the biomolecule along with one or more impurities or other entities.

It is a further object of the present invention to provide a process for purifying a selected biomolecule from a biomolecule containing stream by either having the stream at a given condition or modifying the stream to a given condition and adding a polymer soluble in the stream at that given condition, allowing the solubilized polymer to circulate throughout the stream, changing the given condition of the stream so as to cause the polymer to become insoluble in the stream and bind the desired biomolecule, separating the stream from the polymer and processing the polymer further to recover the desired biomolecule.

It is an object to do the process with an overabundance of polymer and recover all the polymer as a precipitate from the mixture.

It is an additional object of the present invention to provide the process based on a polymer which is soluble based upon a condition selected from temperature, salt, temperature and salt content or pH.

It is another object of the present invention to provide a polymer selected from poly(2 or 4-vinylpyridine), poly(2 or 4-vinylpyridine-co-styrene), (0-50% mol styrene), poly(2 or 4-vinylpyridine-co-methyl methacrylate), (0-50% mol methacrylate), poly(2 or 4-vinylpyridine-co-butyl methacrylate), (0-50% mol methacrylate), Poly(2 or 4-vinylpyridine) grafted hydroxyalkylcellulose, poly(2 or 4-vinylpyridine-co-N-isopropylacrylamide), and poly(methacrylic acid-co-methylmethacrylate).

It is a further object of the present invention to provide a polymer selected from poly(2 or 4-vinylpyridine), poly(2 or 4-vinylpyridine-co-styrene), (0-50% mol styrene), poly(2 or 4-vinylpyridine-co-methyl methacrylate), (0-50% mol methacrylate), poly(2 or 4-vinylpyridine-co-butyl methacrylate), (0-50% mol methacrylate), Poly(2 or 4-vinylpyridine) grafted hydroxyalkylcellulose, poly(2 or 4-vinylpyridine-co-N-isopropylacrylamide), and poly(methacrylic acid-co-methylmethacrylate) and wherein the polymer either has a functional group, such as a carboxylated or pyridine group, or a ligand such as MEP, attached to the polymer that selectively binds to the biomolecule of interest.

It is a further object of the present invention to provide a process for purifying a selected biomolecule from a biomolecule containing mixture by setting the mixture to a given condition, modifying a carrier liquid compatible with the mixture to the same given condition, adding a polymer soluble in the carrier liquid at that given condition to the carrier liquid, allowing the carrier liquid with the solubilized polymer to the mixture and allowing it to circulate throughout the mixture, changing the given condition of the stream so as to cause the polymer to become insoluble in the stream, bind the desired biomolecule, and precipitate out along with or more entities of the mixture, separating the mixture from the polymer and recovering the entity.

It is an additional object of the present invention to provide a static mixer for causing the mixture and solubilized polymer to mix and to allow the polymer to bind to the one or more entities after being precipitated under a different set of ranges of pH, temperature, salt, temperature and salt concentration or the like.

It is another object of the present invention to provide that the one or more entities are a biomolecule in the mixture.

It is an additional object of the present invention to provide a process for the purification of a mixture of biological constituents in a single step.

It is another object of the present invention to provide a process for the purification of a mixture of biological constituents selected from proteins, polypeptides, monoclonal antibodies, humanized, chimeral or animal monoclonal antibodies polyclonal antibodies, antibody fragments, multispecific antibodies, immunoadhesins, and $C_H2/C_H3$ region-containing proteins.

It is a further object of the present invention to provide a process of having a mixture containing a biomolecule of interest at a set range of conditions that will cause one or more polymers of choice to go into solution, adding the one or more polymers and having one or more polymers go into solution, mixing the one or more insoluble polymers with entities of the mixture changing the conditions of the mixture to cause the one or more polymers to precipitate out of solution and then separating the precipitate from the remainder of the mixture, while retaining one or more entities of the mixture to the precipitate for further processing.

It is a further object of the present invention to provide a carrier liquid for the polymer having conditions suitable to cause the polymer to go into solution in the carrier liquid and then to add the carrier liquid with the dissolved polymer to the mixture.

It is an additional object of the present invention to provide one or more static mixers to mix the polymer and the mixture.

It is a further object of the present invention to provide a process for recovering a biomolecule of interest from a clarified mixture obtained from a fermentor or bioreactor in which it has been made.

It is an additional object of the present invention to provide a filtration step to separate the precipitate from the remainder of the mixture.

It is another object of the present invention to provide a normal flow filtration step to separate the precipitate from the remainder of the mixture.

It is a further object of the present invention to provide a tangential flow filtration step to separate the precipitate from the remainder of the mixture.

It is an additional object of the present invention to provide a centrifugation step to separate the precipitate from the remainder of the mixture.

It is another object of the present invention to provide a decantation step to separate the precipitate from the remainder of the mixture.

It is an additional object of the present invention to provide a further step to recover the one or more constituents of the mixture from the precipitated polymer.

It is a further object of the present invention to provide additional processing to the biomolecule of interest.

It is an additional object of the present invention to provide a further step of formulating the biomolecule in a pharmaceutically acceptable carrier and using it for various diagnostic, therapeutic or other uses known for such biomolecules.

It is an object of the present invention to provide a purified biomolecule in one step, directly out of the bioreactor.

It is a further object of the present invention to use a UF step to concentrate the biomolecule after it has been purified and recovered with the precipitation technique.

It is an additional object of the present invention to effect the purification and recovery of a biomolecule with additional processing using an enhanced UF (charged UF) process.

IN THE DRAWINGS

Figure 2:
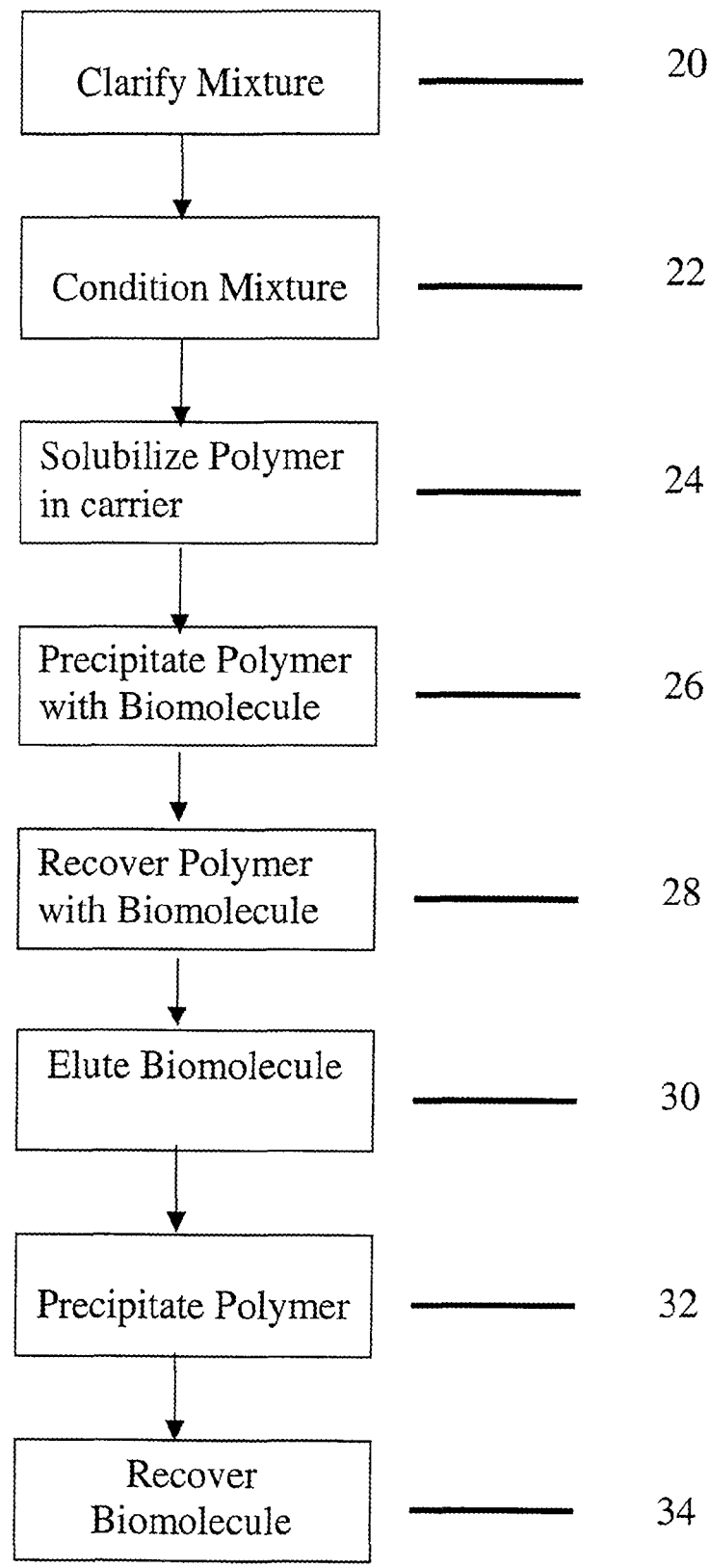
Figure 3:
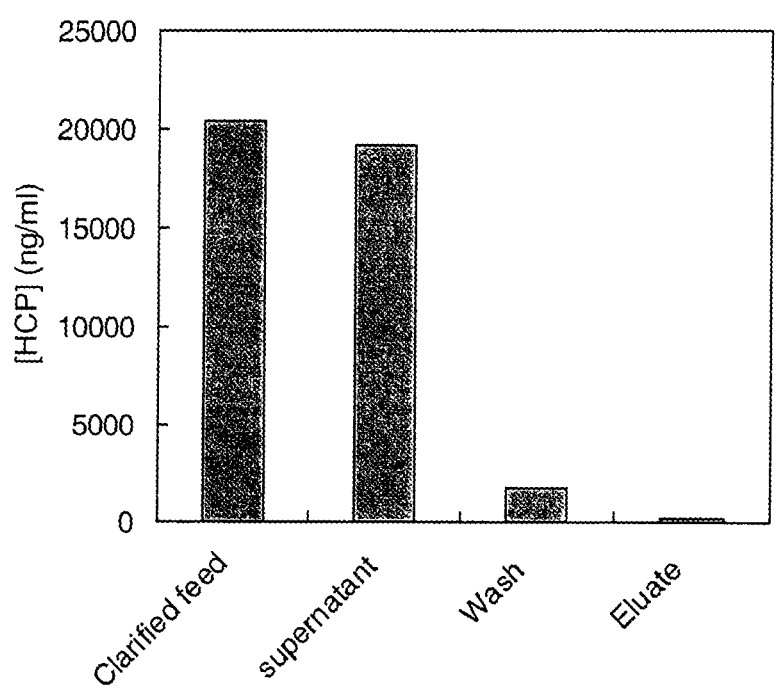
Figure 4:
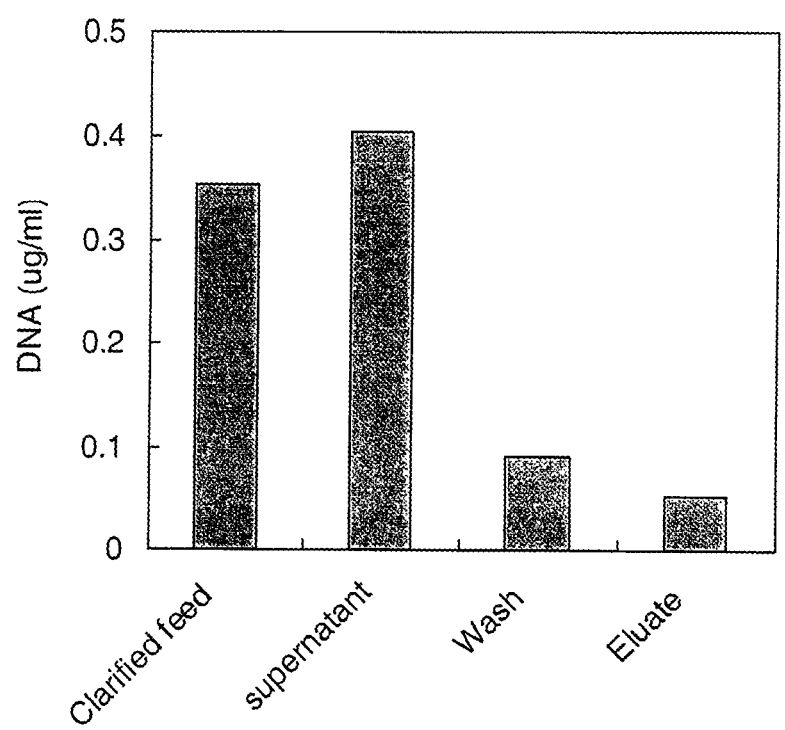

FIG. 1 shows a block diagram of a first process according to the present invention.
FIG. 2 shows a block diagram of a second process according to the present invention.
FIG. 3 shows the data from Example 2 in bar graph form.
FIG. 4 shows the data of Example 3 in bar graph form.

DETAILED DESCRIPTION OF THE INVENTION

The invention is to use a liquid phase or solubilized polymer that has a capability even when precipitated, such as affinity or charge or hydrophobicity and the like, to selectively and reversibly bind to one or more biomolecules of interest. Preferred polymers have electrostatic and hydrophobic ability. The biomolecule of interest is then eluted from the polymer and recovered for further processing.

More specifically, the idea relates to the process of using one or more polymers soluble in a liquid phase to selectively bind to one or more desired biomolecules in a solution/suspension by a precipitation mechanism and which polymer can also be removed, if present, in any excess, by the same mechanism. By way of example, this idea can best be described in the context of protein purification although it can be used to purify any solute from complex mixtures as long as the mechanism of removal applies to the specific solute of interest.

The one or more polymers can be used in excess unlike flocculants and can be recovered essentially completely from the mixture by the precipitation action. This allows one to operate the purification step with greater windows of use and without having to calculate the precise amount of material that needs to be used.

The present concept is based on the fact that certain polymers undergo changes in properties as a result of changes in the environment (stimuli) in which they are in, i.e. stimuli responsive polymers. The most common polymer property to change as a result of a stimulus is solubility and the most common stimuli relating to solubility are temperature, salt concentration and pH. As an example, a polymer may remain in solution as long as the pH, salt level or temperature is maintained within a certain range but it will precipitate out of solution as soon as the condition is changed outside of said range. Certain polymers, such as poly(N-vinyl caprolactam), poly(N-acryloylpiperidine), poly(N-vinylisobutyramide), poly(N-substituted acrylamide) including [poly(N-isopropylacrylamide), poly(N,N'-diethylacrylamide), and poly(N-acryloyl-N'-alkylpiperazine)] and hydroxyalkylcellulose are examples of polymers that exhibit solubility changes as a result of changes in temperature. Other polymers, such as copolymers of acrylic acid and methacrylic acid, polymers and copolymers of 2 or 4-vinylpyridine and chitosan exhibit changes in solubility as a result of changes in pH or salt.

As some of these polymers may not have an ability to selectively bind or elute the desired molecules of interest they need to be modified with ligands or chemical groups that will complex with the desired molecule and hold it in complex and then release the desired molecule under the appropriate elution conditions. Suitable chemical groups can include but are not limited to carboxylated groups and pyridine groups formed as part of the polymer or attached to the polymer. Ligands such as chemical mimics of affinity ligands may be used. Such ligands include but are not limited to natural ligands or synthetic ligands such as mercaptoethylpyridine (MEP), mercaptoethylpyrazine, MEB, 2-aminobenzimidazole (ABI), AMBI, 2-mercapto-benzoic acid (MBA), 4-amino-benzoic acid (ABA), 2-mercapto-benzimidazole (MBI) and the like.

Depending upon the polymer used, the process used can vary.

It is preferred that most of the insoluble impurities, such as cells and cell debris, be removed from the liquid before the capture polymer is used. This may be done by classic methods such as centrifugation of the cell batch and/or clarification through depth filters and the like. Optionally, and preferably, the impurities or at least a portion of the impurities are removed via an impurity removing soluble polymer that is described in our co-pending application, U.S. Ser. No. 60/876,330 filed Dec. 21, 2006. Such polymers can be used in a similar manner to the present invention in that they are dissolved and added to the liquid and precipitated to remove the impurities upon a change in stimuli such as temperature, pH, salt concentration and the like.

Preferred temperature sensitive soluble polymers include but are not limited to functional copolymers of N-isopropylacrylamide, functionalized agarose and functionalized polyethylene oxide.

Preferred pH sensitive soluble polymers include but are not limited to cationic polyelectrolytes and anionic polyelectrolytes. Preferred cationic polyelectrolytes are selected from the group consisting of chitosan, polyvinylpyridines, primary amine containing polymers, secondary amine containing polymers and tertiary amine containing polymers. Preferred anionic polyelectrolytes selected from the group consisting of copolymers of acrylic acid, methacrylic acid and methyl methacrylate.

One preferred method is to remove at least some of the cell mass and larger impurities by filtration, centrifugation or the like and then add one or more of the soluble polymers that are capable of binding to the molecule of interest to the remaining fluid. The fluid may either be preconditioned or the fluid can be conditioned upon addition of the polymer(s) or the polymer(s) can be added to a carrier liquid that is properly conditioned to the temperature or pH or other stimulus. The polymer(s) is allowed to circulate thoroughly with the fluid and then the stimulus is changed (change in pH, temperature, salt concentration, etc) and the desired biomolecule and polymer(s) precipitate out of solution. The desired biomolecule is then recovered from the polymer(s) such as by elution and the like.

Another preferred method is to use an impurity removing polymer system as described in copending application U.S.

Ser. No. 60/876,330 filed Dec. 21, 2006 to remove the impurities without any pretreatment such as clarification, filtration, centrifugation or the like, by adding one or more of the impurity removing soluble polymer(s) such as poly(N-vinyl caprolactam), poly(N-acryloylpiperidine), poly(N-vinylisobutyramide), poly (N-substituted acrylamide) including [poly(N-isopropylacrylamide), poly(N,N'-diethylacrylamide), and poly(N-acryloyl-N'-alkylpiperazine)], hydroxyalkylcellulose, copolymers of acrylic acid and methacrylic acid or methacrylic acid and methyl methacrylate, polymers and copolymers of 2 or 4-vinylpyridine and chitosan to the starting fluid. The fluid may either be preconditioned or the fluid can be conditioned upon addition of the impurity removing polymer(s) or the polymer(s) can be added to a carrier liquid that is properly conditioned to the temperature or pH or other stimulus. The impurity removing polymer(s) is allowed to circulate thoroughly with the fluid and then the stimulus is changed (change in pH, temperature, salt concentration, etc) and the impurities and polymer(s) precipitate out of solution. The remaining liquid that contains the desired molecule and perhaps some amount of impurities (other proteins, viruses, etc) that are not removed by the selected polymer(s) are then recovered such as by filtering it through a suitably sized membrane (microfiltration or ultrafiltration), centrifugation where the desired molecule is in the supernatant that is recovered and the like. This can be conducted in the bioreactor, especially if it is a disposable plastic bioreactor or it can be done in a separate container such as a stainless steel vat or tank or plastic bag, tank or the like.

Then one or more of the soluble polymers that are capable of binding to the molecule of interest is added to the remaining fluid. The soluble binding or capture polymer(s) such as poly(N-vinyl caprolactam), poly(N-acryloylpiperidine), poly (N-vinylisobutyramide), poly (N-substituted acrylamide) including [poly(N-isopropylacrylamide), poly(N,N'-diethylacrylamide), and poly(N-acryloyl-N'-alkylpiperazine)], hydroxyalkylcellulose, copolymers of acrylic acid and methacrylic acid or methacrylic acid and methyl methacrylate, polymers and copolymers of 2 or 4-vinylpyridine and chitosan contain a functional group and/or ligand that binds to the biomolecule of interest. The fluid may either be preconditioned or the fluid can be conditioned upon addition of the polymer(s) or the polymer(s) can be added to a carrier liquid that is properly conditioned to the temperature or pH or other stimulus. The polymer(s) is allowed to circulate thoroughly with the fluid and then the stimulus is changed (change in pH, temperature, salt concentration, etc) and the desired biomolecule and polymer(s) precipitate out of solution. The desired biomolecule is then recovered from the polymer(s) such as by elution The processes will generally involve having one or more conditions of the liquid of the mixture, at the correct pH, temperature or salt concentration or other condition used to cause the polymer(s) to become soluble and then adding the polymer(s) either directly or already solubilized in a carrier liquid, such as water, to the mixture. In many instances, the mixture will be at the proper condition to allow the polymer(s) to be simply added to the mixture.

In other instances, the mixture may need to be conditioned or modified to be at the desired condition. This modification or conditioning can be by modifying the mixture first and then adding the polymer(s), by adding the polymer(s) to a carrier liquid that is conditioned to the desired state and simply adding it to the mixture such that the carrier liquid is sufficient to cause the mixture to thus reach that condition or to do both. The conditions of the liquid in the mixture are then changed (pH, temperature, salt content, combinations thereof, etc) that causes the polymer(s) to become insoluble and precipitate out of the mixture as a dispersed solid suspension. The mixture and the suspended insoluble polymer(s) are then mixed to ensure that the entities of the mixture and the insolubilized polymer(s) have sufficient and intimate contact with each other. The insoluble polymer(s) bind the one or more desired biomolecules it contacted while in the mixture and continue to bind to it thereafter until elution conditions are met to remove the biomolecule from the polymer. The precipitate is separated such as by centrifugation or filtration or gravity and time with the liquid portion being decanted. The recovered polymer/desired biomolecule(s) is washed one or more times to remove any residual impurities or contaminants and then the biomolecule(s) is eluted from the polymer under conditions that cause the biomolecule entity to release from the polymer so it can be recovered and subjected to further processing.

One polymer or a blend of polymers may be used in the present invention and it is meant to cover both embodiments whenever the term polymer, polymer(s) or one or more polymers is used hereafter.

As discussed above, the polymer may be added directly to the mixture either as is or in a conditioned state that enhances the solubility of the polymer as it is added. Alternatively, it can be added to a carrier liquid in which it is soluble and which carrier preferably is also compatible with the mixture. One such carrier liquid is water, water adjusted to a specific pH using acid or base, another is an aqueous based solution such as saline, physiological buffers or blends of water with an organic solvent such as water/alcohol blends. The selection of carrier liquid is dependent on the mixture to which it is added as to what is preferred and tolerated. The polymer is added to the carrier liquid that either has already been conditioned (such as pH adjusted or heated to a desired temperature or heated to a desired temperature with the addition of one or more salts or cooled to the desired temperature with or without one or more salts) or it can be added and then the carrier is conditioned to cause the solubilizing of the polymer in the carrier. The carrier/soluble polymer blend is then added to the mixture.

The mixture may be contained in a mixing vessel such as a tapered bottom metal (preferably stainless steel more preferably 304 or 316L stainless steel) or glass or plastic bag, vat or tank. Alternatively, especially when a cell culture or microbial or yeast culture, it may be the bioreactor or fermentor in which the cells have been grown. It may also be a disposable bioreactor or fermentor or a disposable mixing bag such as a plastic bag as is available from Millipore Corporation of Billerica, Mass. The mixture and polymer are brought into intimate contact through a mixing action that may be done by a magnetic stirred bar, a magnetic driven mixer such as a NovAseptic® mixer available from Millipore Corporation of Billerica, Mass., a Lightning-type mixer, a recirculation pump, or a rocking motion closed mixing bag or bioreactor or fermentor, such as is shown in US 2005/0063259A1 or an airlift type of mixer or reactor in which rising bubbles in the liquid cause a circulatory pattern to be formed.

Alternatively, the mixture and polymer (either by itself or in a carrier) can be in separate containers and mixed in line in a static blender. The blend can either then go to a container or to a centrifuge or a filter where the precipitated polymer and its bound one or more entities is separated from the remainder of the mixture and then is further processed.

In another embodiment, the mixture and polymer (either by itself or in a carrier) are blended together in the container holding the mixture and further mixed in line in a static blender. The blend can either then go to a container or to a centrifuge or to a filter where the precipitated polymer and its bound one or more entities is separated from the remainder of the mixture. Then the precipitated polymer (whichever contains the target or desired biomolecule) is further processed.

Using centrifugation, one can easily and quickly separate the precipitated polymer from the remainder of the liquid mixture. After centrifugation, the supernatant, generally the remainder of the mixture is drawn off. The precipitated polymer is further processed. If desired the supernatant may be subjected to one or more additional polymer precipitation steps to recover even more of the desired biomolecule.

Simple decantation may also be used if desired.

Filtration can be accomplished in a variety of manners. Depending upon the size of the polymer as it is precipitated; one may use one or more filters of varying sizes or asymmetries. The selection of type and size of filter will depend on the volume of precipitate to be captured.

Membrane based filters, preferably microporous membranes can be used in the present invention. Such filters are generally polymeric in nature and can be made from polymers such as but not limited to olefins such as polyethylene including ultrahigh molecular weight polyethylene, polypropylene, EVA copolymers and alpha olefins, metallocene olefinic polymers, PFA, MFA, PTFE, polycarbonates, vinyl copolymers such as PVC, polyamides such as nylon, polyesters, cellulose, cellulose acetate, regenerated cellulose, cellulose composites, polysulfone, polyethersulfone, polyarylsulfone, polyphenylsulfone, polyacrylonitrile, polyvinylidene fluoride (PVDF), and blends thereof. The membrane selected depends upon the application, desired filtration characteristics, particle type and size to be filtered and the flow desired. Preferred membrane based filters include DURAPORE® PVDF membranes available from Millipore Corporation of Billerica Mass., MILLIPORE EXPRESS® and MILLIPORE EXPRESS® PLUS or SH PES membranes available from Millipore Corporation of Billerica Mass.

Depending on the mixture, polymer and the nature of biomolecule may be hydrophilic or hydrophobic. Preferred membranes are hydrophilic and are low in protein binding.

The membrane may be symmetric in pore size through out its depth such as DURAPORE® PVDF membranes available from Millipore Corporation of Billerica Mass., or it may be asymmetric in pore size through its thickness as with MILLIPORE EXPRESS® and MILLIPORE EXPRESS® PLUS or SH PES membranes available from Millipore Corporation of Billerica Mass. It may contain a prefilter layer if desired, either as a separate upstream layer or as an integral upstream portion of the membrane itself.

The pore size of the membrane can vary depending upon the polymer and mixture selected. Generally, it has an average pore size of from about 0.05 micron to 5 microns, preferably from about 0.05 micron to about 1 micron, more preferably from about 0.05 to about 0.65 micron.

The membrane filter may run in a deadend or normal flow (NF) format or a tangential flow (TFF) format. The choice is dependent on a number of factors, primarily the user's preference or installed filtration equipment as either works with the present invention. A TFF process and equipment is preferred when large amounts of polymer and molecule are to be recovered as TFF is less subject to clogging or fouling than NF methods.

FIG. 1 shows a block diagram of a first process of the present invention. In the first step 2, the clarified mixture is either conditioned to the correct parameter(s) to maintain the capture polymer of choice in solution or if the conditions of the mixture are already such that the polymer(s) become soluble in the mixture, no further conditioning may be required. Alternatively, the polymer(s) may be added as a solid to an unconditioned mixture and then the mixture (containing the solid polymer(s)) may be conditioned to the correct parameters to dissolve the capture polymer(s) in the mixture. In the second step 4, the polymer(s) is mixed with the mixture in the stream for desirable amount of time to create suitable distribution to make intimate contact with all the constituents of the mixture. In the third step 6, the conditions of the liquid in the mixture are then changed (pH, temperature, salt content, combinations thereof, etc) to cause the polymer(s) to become insoluble and precipitate out of the mixture as a dispersed solid suspension while retaining the biomolecule. The mixture and the precipitated polymer(s) are then separated from each other in the fourth step 8. As discussed above the precipitate and remaining mixture may be separated by centrifugation or filtration.

The precipitate can then optionally be washed one or more times with water, a buffer or an intermediate wash solution as are known in the art to remove any impurities from the precipitate or any non-specifically bound impurities from the precipitate.

The desired biomolecule is then recovered. Preferably it eluted from the polymer such as by the addition of a buffer at a pH (acidic or basic depending on the molecule and the polymer used) and the salt concentration or temperature of the solution is changed to allow for the recovery of the desired molecule free of the polymer in step 10.

FIG. 2 shows a block diagram of this process as applied to a pH dependent polymer such as poly(4-vinylpyridine-co-styrene), (10% mol styrene) which has an affinity for the desired biomolecule in the insoluble state. In the first step 20, the mixture is clarified from a harvested broth so as to remove most of the insoluble impurities such as cells, cell debris and the like. The mixture is then either conditioned to the correct pH (in this case to a pH below about 5.0) to maintain the polymer of choice in solution before, during or after the introduction of the polymer or it is already at the desired condition in a second step 22. In the third step 24 which may occur separately before, simultaneously or after the second step 22, the polymer is added to a carrier liquid under conditions that allow it to go into solution and then mixed to make intimate contact with all the constituents of the mixture so that the polymer can complex with the desired molecule (for example a IgG molecule).

In the fourth step 26, the mixture conditions are changed to cause the polymer to precipitate out of solution in the form of a dispersed solid suspension If desired one may conduct one or more additional steps to ensure that all polymer has been removed from the mixture by subjecting the mixture to a step containing a material that will remove any residual polymer from the mixture such as ion exchange resin, activated carbon, alumina, diatomaceous earth and the like. Typically however the polymer is removed on the first precipitation and such additional steps are not necessary.

As discussed above the precipitate and remaining mixture may be separated by centrifugation or filtration in a fifth step 28. Optionally, the polymer and complex are washed one or more times while being kept under conditions such that the polymer/complex precipitate remains undissociated.

To recover the molecule, the conditions are changed, such as by lowering the pH of the solution, so as to solubilize the polymer and to break the complex between the ligand and the molecule in the sixth step 30. In the seventh step 32, the solution conditions are changed, such as by increasing the ionic strength to selectively cause the polymer to precipitate out of the solution, thereby leaving substantially all of the biomolecule of interest in solution. The supernatant (liquid) is removed from the precipitated polymer by filtration or centrifugation or the like and is recovered in the eighth step 34.

The biomolecule of interest after having been recovered, may undergo one or more known additional process steps such as chromatography steps including but not limited to ion exchange, hydrophobic interaction or affinity chromatography, various filtration steps such as microfiltration ultrafiltration, high performance tangential flow filtration (HPTFF) with or without charged UF membranes, viral removal/inactivation steps, final filtration steps and the like. Alternatively, the eluted biomolecule of interest may be used as is without the need for further purification steps. Also the biomolecule of interest may undergo further purification without the need for chromatography steps.

In a further embodiment, it eliminates all process steps after cell harvest/clarification through affinity chromatography. A biological process under this embodiment would consist of capture of the biomolecule directly from the clarified mixture via the polymer-based purification step, separation of the biomolecule from the polymer and the remainder of the mixture, two or more steps of viral removal or inactivation such as removal through viral filters or inactivation through treatment with heat, chemicals or light, a compounding step into the correct formulation and a final filtering before filling the compounded biomolecule into its final container for use (vial, syringe, etc).

In any of the embodiments of the present invention the biomolecule such as a protein thus recovered may be formulated in a pharmaceutically acceptable carrier and is used for various diagnostic, therapeutic or other uses known for such molecules.

The mixture that is the starting material of the process will vary depending upon the cell line in which it was grown as well as the conditions under which it is grown and harvested. For example, in most CHO cell processes the cells express the molecule outside of the cell wall into the media. One tries not to rupture the cells during harvest in order to reduce the amount impurities in the mixture. However, some cells during grow and harvesting may rupture due to shear or other handling conditions or die and lyse, spilling their contents into the mixture. In bacteria cell systems, the biomolecule is often kept with the cellular wall or it may actually be part of the cellular wall (Protein A). In these systems the cell walls need to be disrupted or lysed in order to recover the biomolecule of interest.

The target molecule to be purified can be any biomolecule, preferably a protein, in particular, recombinant protein produced in any host cell, including but not limited to, Chinese hamster ovary (CHO) cells, Per.C6® cell lines available from Crucell of the Netherlands, myeloma cells such as NSO cells, other animal cells such as mouse cells, insect cells, or microbial cells such as E. coli or yeast. Additionally, the mixture may be a fluid derived from an animal modified to produce a transgenic fluid such as milk or blood that contains the biomolecule of interest. Optimal target proteins are antibodies, immunoadhesins and other antibody-like molecules, such as fusion proteins including a $C_H2/C_H3$ region. In particular, this product and process can be used for purification of recombinant humanized monoclonal antibodies such as (RhuMAb) from a conditioned harvested cell culture fluid (HCCF) grown in Chinese hamster ovary (CHO) cells expressing RhuMAb.

Antibodies within the scope of the present invention include, but are not limited to: anti-HER2 antibodies including Trastuzumab (HERCEPTIN®) (Carter et al., *Proc. Natl. Acad. Sci. USA*, 89:4285-4289 (1992), U.S. Pat. No. 5,725,856); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108, B1, or Tositumomab (BEXXAR®); anti-IL-8 (St John et al., *Chest,* 103:932 (1993), and International Publication No. WO 95/23865); anti-VEGF antibodies including humanized and/or affinity matured anti-VEGF antibodies such as the humanized anti-VEGF antibody huA4.6.1 AVASTIN®. (Kim et al., *Growth Factors,* 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., *Transplant Intl.* 4:3-7 (1991), and Hourmant et al., *Transplantation* 58:377-380 (1994)); anti-IgE (Presta et al., *J Immunol.* 151: 2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-α antibodies including cA2 (REMICADE®), CDP571 and MAK-195 (See, U.S. Pat. No. 5,672,347 issued Sep. 30, 1997, Lorenz et al. *J. Immunol.* 156(4):1646-1653 (1996), and Dhainaut et al. *Crit. Care Med.* 23(9):1461-1469 (1995)); anti-Tissue Factor (TF) (European Patent No. 0 420 937 B1 granted Nov. 9, 1994); anti-human $\alpha_4\beta_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al. *Arthritis Rheum* 39(1):52-56 (1996)); anti-CD52 antibodies such as CAMPATH-1H (Riechmann et al. *Nature* 332: 323-337 (1988)); anti-Fc receptor antibodies such as the M22 antibody directed against FcγR1 as in Graziano et al. *J. Immunol.* 155(10):4996-5002 (1995); anti-carcinoembryonic antigen (CEA) antibodies such as hMN-14 (Sharkey et al. *Cancer Res.* 55(23 Suppl): 5935s-5945s (1995); antibodies directed against breast epithelial cells including huBrE-3, hu-Mc 3 and CHL6 (Ceriani et al. *Cancer Res.* 55(23): 5852s-5856s (1995); and Richman et al. *Cancer Res.* 55(23 Supp): 5916s-5920s (1995)); antibodies that bind to colon carcinoma cells such as C242 (Litton et al. *Eur J. Immunol.* 26(1):1-9 (1996)); anti-CD38 antibodies, e.g. AT 13/5 (Ellis et al. *J Immunol.* 155(2):925-937 (1995)); anti-CD33 antibodies such as Hu M195 (Jurcic et al. *Cancer Res* 55(23 Suppl):5908s-5910s (1995) and CMA-676 or CDP771; anti-CD22 antibodies such as LL2 or LymphoCide (Juweid et al. *Cancer Res* 55(23 Suppl):5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIRQ anti-CA 125 antibody OvaRex; anti-idiotypic GD3 epitope antibody BEC2; anti-αvβ3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

Aside from the antibodies specifically identified above, the skilled practitioner could generate antibodies directed against an antigen of interest, e.g., using the techniques described below.

The antibody herein is directed against an antigen of interest. Preferably, the antigen is a biologically important polypeptide and administration of the antibody to a mammal suffering from a disease or disorder can result in a therapeutic benefit in that mammal. However, antibodies directed against non-polypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those proteins described in section (3) below. Exemplary molecular targets for antibodies encompassed by the present invention include CD proteins such as CD3, CD4, CD8, CD19, CD20, CD22, CD34, CD40; members of the ErbB receptor family such as the EGF receptor, HER2, HER3 or HER4 receptor; cell adhesion molecules such as LFA-1, Mac1, p150,95, VLA-4, ICAM-1, VCAM and αvβ3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C, or any of the other antigens mentioned herein. Antigens to which the antibodies listed above bind are specifically included within the scope herein.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Other antigens and forms thereof useful for preparing antibodies will be apparent to those in the art.

Polyclonal antibodies can also be purified in the present invention. Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N$—C—NR, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are of interest in the present invention and may be made using the hybridoma method first described by Kohler et al., *Nature*, 256:495 (1975), or may be made by recombinant DNA methods (U.S. Pat. No. 4,816, 567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Pro-Sep® Protein A media available from Millipore Corporation of Billerica, Mass., hydroxyapatite chromatography, gel electrophoresis, dialysis, or affinity chromatography. Preferably the Protein A chromatography procedure described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In a further embodiment, monoclonal antibodies can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional hybridoma techniques for isolation of monoclonal antibodies.

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239: 1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.,* 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci.* USA, 90:2551 (1993); Jakobovits et al., *Nature,* 362:255-258 (1993); Bruggermann et al., *Year in Immuno.,* 7:33 (1993); and Duchosal et al. Nature 355:258 (1992). Human antibodies can also be derived from phage-display libraries (Hoogenboom et al., *J. Mol. Biol.,* 227:381 (1991); Marks et al., *J. Mol. Biol.,* 222:581-597 (1991); Vaughan et al. *Nature Biotech* 14:309 (1996)).

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science,* 229: 81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J Exp. Med.,* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells over expressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994). Alternatively, the antibodies can be "linear antibodies" as described in Zapata et al. *Protein Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are contemplated. For example, trispecific antibodies can be prepared. Tutt et al. *J. Immunol.* 147: 60 (1991).

The simplest and most straightforward immunoadhesin design combines the binding domain(s) of the adhesin (e.g. the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc domain of immunoglobulin G$_1$ (IgG$_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:
(a) $AC_L$-$AC_L$;
(b) $AC_H$-($AC_H$, $AC_L$-$AC_H$, $AC_L$-$V_H C_H$, or $V_L C_L$-$AC_H$);
(c) $AC_L$-$AC_H$-($AC_L$-$AC_H$, $AC_L$-$V_H C_H$, $V_L C_L$-$AC_H$, or $V_L C_L$-$V_H C_H$)
(d) $AC_L$-$V_H C_H$-($AC_H$, or $AC_L$-$V_H C_H$, or $V_L C_L$-$AC_H$);
(e) $V_L C_L$-$AC_H$-($AC_L$-$V_H C_H$, or $V_L C_L$-$AC_H$); and
(f) $V_L C_L$-$V_H C_H)_2$,
wherein each A represents identical or different adhesin amino acid sequences;
$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H 2$ domain, or between the $C_H 2$ and $C_H 3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell* 61:1303-1313 (1990); and Stamenkovic et al., *Cell* 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

In other embodiments, the protein to be purified is one which is fused to, or conjugated with, a $C_H 2$/$C_H 3$ region. Such fusion proteins may be produced so as to increase the serum half-life of the protein. Examples of biologically important proteins which can be conjugated this way include renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD34, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

The following examples are offered by way of illustration and not by way of limitation. The disclosures of all citations in the specification are expressly incorporated herein by reference.

EXAMPLES

Example 1

This Example Illustrates the Capture of Monoclonal Antibody from a Clarified Feed Using Poly(4-Vinyl Pyridine-Co-Styrene) (10 Mol % Styrene)

0.1 g of the polymer (10% wt in 1 M HCl) was added to 10 ml of clarified I feedstock containing an anti-NIP antibody (pH 4.0) and mixed at room temperature for 10 min. The polymer was then precipitated by adjusting the pH of the mixture to around 7.0. The precipitate, in the form of a dispersed solid suspension, was mixed continuously for 30 min in the clarified feed to allow for complexation with the desired product. The precipitate was then collected by centrifugation (4000 rpm for 1 min) and washed with DI water to remove adhering impurities. Re-solubilization of the precipitate and elution of the product took place at pH 3.0. Reprecipitation and removal of the free polymer was affected by adding 100 mM sodium perchlorate followed by filtration through 5 and 0.2μ Millex® filters available from Millipore Corporation of Billerica, Mass.

Following this procedure, ≥95% of the monoclonal antibody could be recovered from the clarified feed. The binding capacity of the smart polymer was 0.4-0.5 mg monoclonal antibody/mg polymer with an observed recovery of 80-85%.

Example 2

This Example Illustrates the Purity of a Solution Containing a Desired Biomolecule that was Captured Using Poly(4-Vinyl Pyridine-Co-Styrene)

The feed of Example 1 was used in this example.

0.1 g of the polymer (10% wt in 1 M HCl) was added to 10 ml of clarified feed (pH 4.0) and mixed at room temperature for 10 minutes. The polymer was then precipitated by adjusting the pH of the mixture to around 7.0. The precipitate, in the form of a dispersed solid suspension, was mixed continuously for 30 min in the clarified feed to allow for complexation with the desired product. The precipitate was then collected by centrifugation (4000 rpm for 1 min) and washed with DI water to remove adhering impurities. Re-solubilization of the precipitate and elution of the product took place at pH 3.0. Removal of the free polymer was affected by adding 100 mM sodium perchlorate followed by filtration through 5 and 0.2μ Millex® filters.

An ELISA assay kit (Cygnus CM015, lot17077) was used to follow the level of host cell protein (HCP) at different steps of the product capture process. The antibodies used in this ELISA were not raised against the specific strain used here. It is possible that the sample contains HCP that is not detected with the polyclonal antibody provided in the kit.

As illustrated in FIG. 3, in the capture step, most of the HCP remains in the supernatant which contains 19,000 ppm. A further 1800 ng/mL of HCP are released during the wash step. In the eluant, HCP levels are reduced to 154 ng/mL.

Example 3

This Example Illustrates the Level of DNA in a Solution Containing a Desired Biomolecule that was Captured Using Poly(4-Vinyl Pyridine-Co-Styrene)

The experiment was carried out as illustrated in example 2. The quantification of DNA in the different steps of the capture process was carried out by Pico-Green assay. Each sample was assayed using several dilution factors to assess dilution recovery. In addition, DNA was spiked into each sample to increase the concentration by 0.1 ug/mL, and spike recovery was assessed at each dilution. Good dilution recovery was observed for most of the samples, and spike recoveries were generally within the acceptable range (75%-150%).

As depicted in FIG. 4, the levels of DNA in the clarified feed and eluant were 0.4 ug/mL and 0.05 ug/mL respectively. Thus, the eluant from the capture process contains ~10-fold less DNA.

Example 4

This Example Illustrates the Synthesis of poly(N-isopropylacrylamide)-co-mercaptoethylpyridine, (PNIPAM-co-MEP) Polymer and Ligand To N-isopropylacrylamide (NIPAAM) (7.11 g, 62.8 mmol) and glycydylmethacrylate (GMA) (2.91 g, 20.41 mmol) in tertiary butanol (tBuOH) at 30° C. under nitrogen is added an initiator, VAZO® 88 (54 mg, 0.22 mmol). Nitrogen was bubbled through this mixture for 10 minutes. The solution was then heated at 80° C. for 2 days. TLC analysis (97:3 MDC:MeOH) showed no polymer, only monomer. Hence initiator (57 mg) was added and the mixture again heated at 80° C. for 18 hours. TLC analysis revealed no monomer present with the solution becoming viscous. The solution was transferred with the aid of tetrahydrofuran (THF) and the solvents were removed under reduced pressure to yield a colorless syrup (12.95 g). This material was purified by precipitation as follows. The material was dissolved in THF (30 ml) with heating to 35° C. then precipitated with ethylene oxide (Et2O) (200 ml). This procedure was repeated 2 times more. The white latex product was dried under vacuum (14 mbar) at 40° C. to yield a whites solid which was ground up (9.69 g).

To p(NIPAAM)-GMA activated polymer (1.28 g, at 2 mmol/g) in THF (30 ml) and water (30 ml) under a nitrogen atmosphere was added mercaptoethylpyridine (MEP) HCl (921 mg, 5.2 mmol) followed by 10M sodium hydroxide (NaOH) (1.3 ml). The reaction was stirred at ambient temperature for 18 hours. A color change was noted. 2-mercaptoethanol (1 ml) was added to block any unreactive epoxide groups. The reaction was warmed to 35° C. for 1 hour. The THF was removed under reduced pressure and water was added (100 ml). The pH was adjusted to 2 with 0.5M HCl. A solution resulted. This solution was subjected to ultrafiltration on a UF 1 KD regenerated cellulosic membrane (PLAC) available from Millipore Corporation of Billerica, Mass.

After a total of 750 ml of permeate collected the water was removed under reduced pressure to yield a colorless glass like material (870 mg). A sample was submitted for elemental analysis which gave a ligand density of 1.3 mmol/g based on S analysis.

Example 5

This Example Illustrates the Synthesis of Poly(N-Isopropylacrylamide)-Co-2-Aminobenzimidazole (PNIPAM-Co-ABI) Polymer and Ligand To NIPAM (10.06 g, 88.9 mmol) and N-acryloxysuccinimide (NAS) (380 mg, 2.2 mmol) under nitrogen was added inhibitor free THF (25 ml) and toluene (25 ml). Nitrogen was bubbled through the solution for 5 minutes. The stirred reaction mixture was heated at 50° C. and free radical initiator 1,1'-azobis(cyanocyclohexane) VAZO® 88 was added (30 mg, 0.12 mmol, 0.3% by wt). The reaction was heated to 71-73° C. over 15 minutes. The reaction was further heated at this temperature for 18 hours. After this time, the solution appeared more viscous. The reaction mixture was cooled to ambient and a TLC test indicated a small amount of monomer present. The polymer was precipitated by the addition of hexane (100 ml). The white polymer is filtered off and dried under vacuum (20 mbar) to yield p(NIPAM-NAS) copolymer. (10.01 g).

2-aminobenzimidazole (ABI) (292 mg, 2.2 mmol) was dissolved in THF (10 ml) and water (20 ml), p(NIPAAM-NAS) (1.01 g, 0.2 mmol activated) was added and the mixture vigorously stirred for 18 hours. The pH was 9.8. The reaction mixture was filtered through filter paper and made acid with 0.025M HCl (20 ml). The solution was subjected to ultrafiltration using a 1 kD membrane with 4×75 ml of DI water. The water was stripped under reduced pressure (50° C., 20 mbar) to yield a colorless glass like solid (604 mg).

Example 6

This Example Illustrates the Capture of an Antibody Molecule from a Clarified Feedstock Using poly(N-isopropylacrylamide)-co-mercaptoethylpyridine, (PNIPAM-co-MEP)

A 10% wt solution of poly(N-isopropylacrylamide)-co-mercaptoethylpyridine, (PNIPAM-co-MEP) is prepared by dissolving 10 g of the polymer from example 4 in 90 g 1 M hydrochloric acid. 1 g of the polymer solution (10% wt in 1 M HCl) is added to 10 ml of a clarified feedstock containing an anti-NIP antibody molecule. The pH of the feedstock hasd previously been adjusted to 4.0 by the addition of hydrochloric acid. The feedstock, containing the polymer solution, is then mixed at room temperature for 10 min. The polymer is then precipitated by adjusting the pH of the mixture to around 7.0 by the addition of sodium hydroxide. The precipitate, in the form of a dispersed solid suspension, is mixed continuously for 30 minutes to allow for the complexation with the antibody molecule. The precipitate is then collected by centrifugation (4000 rpm for 1 min) and washed with DI water to remove adhering impurities. Re-solubilization of the precipitate and elution of the product is effected by adjusting the pH to 3.0 by the addition of hydrochloric acid. Removal of the free polymer is affected by adding 100 mM sodium perchlorate, which precipitates the polymer without rebinding of the biomolecule to it, followed by filtration through 5 and 0.2 μm Millex® filters available from Millipore Corporation of Billerica, Mass. The purified anti-NIP antibody molecule is then recovered in the supernatant fluid.

Example 7

This Example Illustrates the Capture of an Antibody Molecule from a Clarified Feedstock Using Poly(Methyl Methacrylate-Co-Methacrylic Acid)

A 10% wt solution of poly(methyl methacrylate-co-methacrylic acid) is prepared by dissolving 10 g of the polymer, obtained from Sigma-Aldrich Company, in water while adjusting the pH to 10 by the addition of sodium hydroxide. 1 g of the polymer solution (10% wt in 1 M HCl) is added to 10 ml of a clarified feedstock containing an anti-NIP antibody molecule. The feedstock solution, containing the polymer solution, is then mixed at room temperature for 5 minutes. The pH of the resulting solution is then adjusted to 4 to effect the complexation of the polymer to the antibody molecule, the solution is mixed at room temperature for 10 minutes. The pH of the solution is then adjusted to 2.5 by the addition of hydrochloric acid to precipitate the polymer. The removal of the solid polymer is effected by filtration through 5 and 0.2 μm Millex® filters available from Millipore Corporation of Billerica, Mass. Analysis of the supernatant filtrate shows no evidence of the antibody molecule, it is all been captured by the polymer.

What is claimed:

1. A method for purifying an IgG antibody produced in a microbial host cell, the method comprising the steps of:
    a. providing a mixture comprising an IgG antibody produced in a microbial host cell;
    b. adding one or more stimuli responsive polymers to the mixture under pH conditions such that the one or more polymers are solubilized and are capable of reversibly and selectively binding to the IgG antibody, said one or more polymers being one or more polyvinyl pyridine-containing polymers;
    c. mixing the one or more solubilized stimuli responsive polymers throughout the mixture;
    d. changing the pH conditions such that to precipitate the one or more polymers and bound IgG antibody out of solution; and
    e. separating the precipitated polymer and bound IgG antibody from the mixture.

2. The method of claim 1, further comprising the step of recovering the bound IgG antibody from the polymer.

3. The method of claim 1, wherein the microbial host cell is a yeast cell.

4. The method of claim 1, wherein the microbial host cell is an *E. coli* cell.

* * * * *